United States Patent [19]
Bacus et al.

[11] Patent Number: 5,541,064
[45] Date of Patent: Jul. 30, 1996

[54] METHODS AND APPARATUS FOR IMMUNOPLOIDY ANALYSIS

[75] Inventors: James W. Bacus, Hinsdale; Robert J. Marder, River Forest, both of Ill.

[73] Assignee: Cell Analysis Systems, Inc., Franklin Lakes, N.J.

[21] Appl. No.: 137,713

[22] Filed: Oct. 15, 1993

Related U.S. Application Data

[62] Division of Ser. No. 831,010, Feb. 5, 1992, Pat. No. 5,281,517, which is a continuation of Ser. No. 320,274, Mar. 7, 1989, abandoned, which is a division of Ser. No. 121,674, Nov. 17, 1987, Pat. No. 5,016,283, which is a continuation-in-part of Ser. No. 927,285, Nov. 4, 1986, Pat. No. 5,018,209, which is a continuation-in-part of Ser. No. 794,937, Nov. 4, 1985, Pat. No. 4,741,043.

[51] Int. Cl.$^6$ ..................................... C12M 3/00
[52] U.S. Cl. .............. 435/6; 435/7.200; 435/7.230; 436/10; 436/63; 436/64; 422/68.100; 356/39; 356/318; 356/320; 364/413.080; 364/413.100; 382/129; 382/133; 382/134
[58] Field of Search .................. 435/6, 7.2, 7.23; 436/10, 63, 64; 422/68.1; 382/6, 38, 129, 133, 134; 356/39, 318, 320; 364/497, 413.22, 413.08, 413.1

[56] References Cited

U.S. PATENT DOCUMENTS 4,998,284  3/1991  Bacus et al. .................. 382/6
5,134,662  7/1992  Bacus et al. .................. 382/6

OTHER PUBLICATIONS

R. Riley, "Cellular Proliferation Markers In the Evaluation of Human Cancer," Clinics In Laboratory Medicine, vol. 12, No. 2 (1992) 163–199.

B. Schwartz et al, "Cell Proliferation in Non–Hodgkin's Lymphoms Digital Image Analysis of Ki67 Antibody Staining", Am. J. Pathol vol. 134, No. 2 (1989) 327–336.

*Primary Examiner*—Carol A. Spiegel
*Attorney, Agent, or Firm*—Allen W. Wark

[57] ABSTRACT

A method and apparatus are provided for selecting and analyzing a subpopulation of cells or cell objects for a certain parameter such as DNA using image analysis means. The cells are first stained with an alkaline phosphatase technique including a monoclonal antibody specific to a protein in at least one of the cell's cytoplasm or on a cell membrane, thereby marking any cells including the protein as to type. A second staining of the DNA in the nucleus is accomplished by a Feulgen technique that destroys the cell cytoplasm. After the staining and marking, the cells may then be gated using the image analysis means on the visual parameter such as colored DNA or colored antigen into a subpopulation that is to be measured. The selected cells may then be examined by digital image processing and measured for a parameter such as a true actual measurement of DNA in picograms. A quantitation of the measured parameter may be generated and provided.

5 Claims, 15 Drawing Sheets

METHODS AND APPARATUS FOR IMMUNOPLOIDY ANALYSIS

CROSS REFERENCE TO RELATED APPLICATIONS

This application is a division of application U.S. Ser. No. 831,010, Feb. 5, 1992, U.S. Pat. No. 5,281,517, which is a continuation of application U.S. Ser. No. 320,274, Mar. 7, 1989, abandoned, which is a division of application U.S. Ser. No. 121,674, Nov. 17, 1987, U.S. Pat. No. 5,016,283, which is a continuation in part of application U.S. Ser. No. 927,285 filed Nov. 4, 1986 U.S. Pat. No. 5,018,509, in the name of James W. Bacus and entitled "Analysis Method and Apparatus for Biological Specimens" which in turn is a continuation-in-part of application U.S. Ser. No. 794,937 filed Nov. 4, 1985, U.S. Pat. No. 4,741,043 in the name of James W. Bacus and entitled "Cell Analysis Apparatus and Method With Calibration and Control Slide", both of which are commonly assigned with the present application. These previous disclosures of Bacus are hereby expressly incorporated by reference herein.

FIELD OF THE INVENTION

The invention relates generally to the measurement of cell object features and other parameters by image analysis, and is more particularly directed to quantitative measurement methods and apparatus for DNA analysis of small cell populations.

BACKGROUND OF THE INVENTION

The present invention is directed to quantitative testing apparatus and methods which may be used for a wide range of diagnostic and prognostic evaluations of various cells, antigens, or other biological materials taken from the human body. However, for purposes of illustration and ease of understanding, the invention will be disclosed in conjunction with its preferred use, which is the quantitative measurement of cellular DNA for the purpose of cancer diagnosis and prognosis. More specifically, the present invention is directed to methods and apparatus for interactive image analysis which are adapted to analyze and quantify the DNA in different classes of specimen cells taken from a human body.

The current state of the art in the pathology laboratory for measuring the DNA content of a cell is by visual observation. A pathologist observes through a microscope primarily the shape and texture of suspected cancer cells and then classifies the cells into a normal category or into one of several abnormal or cancer categories. Such evaluations are very subjective and can not differentiate and precisely quantify small changes in DNA within individual cells or in very small populations of abnormal cells. These small changes may represent an incipient stage of cancer or a change in cell structure due to treatment of the cancer by chemotherapy or radiation. Such small changes are, therefore, important in the diagnosis and prognosis of these diseases.

However, the advantage in diagnosis and/or prognosis of abnormal ploidy distributions that a pathologist viewing a specimen under a microscope has is the discerning expertise of a skilled person in classifying cells as normal or abnormal. There is an innate human ability to make relatively quick infinite gradations of classification, i.e., almost normal, slightly abnormal, etc. On the other hand, the classification and measurement of cell features and parameters manually by a pathologist on a cell-by-cell basis is extremely tedious and time consuming. Statistical analysis of such cell data taken by hand is relatively difficult because each record has to be entered and then processed. For different records, taken at different times, and under varying conditions broad statistical categorizations may be unreliable.

The alternative is automated cell analysis where the pathologist uses specialized equipment to perform the analysis. In automatic cell analysis, such as that accomplished by a flow cytometer, mass tests are performed in gross on a specimen cell population without a researcher being able to exclude or include certain data of the population. The specimen is measured "as is" without really knowing what cells are being measured and how many. Important single cell data or data from relatively small groups of cells are lost in the overall averaging of a specimen. Further, relatively large amounts of a specimen have to be used to provide results from these tests and the sample is consumed.

Although there are commercially available general purpose flow cytometers, they are very expensive and can handle only liquid blood specimens or tissue disaggregations. These cytometers are incapable of working on standard tissue sections or using conventional microscope slides which are the preferred specimen forms of pathology laboratories. Additionally, a flow cytometer does not allow for the analysis of morphological features of cells such as texture, size and shape of cell nuclei and alterations in the nuclear-to-cytoplasmic ratios of cells.

The methods and apparatus illustrated in the referenced Bacus applications have solved these and other problems relating to the analysis of various features and parameters of cell objects. Bacus discloses a measurement method and apparatus which can acquire accurate quantitative data concerning a plurality of individual cells very quickly by an interactive process with a pathologist or an operator.

The Bacus apparatus provides means for displaying on a video monitor an image of a group of cells from a field of a microscope slide. The image is further digitized and stored in a memory of the apparatus. From the digitized image, a processor means identifies each possible cell object automatically by a pattern recognition technique. An interactive program allows the operator to point to each object or cell in succession and make morphological decisions for classification and measurements concerning each. For quantitative DNA analysis, the measurement is of the optical density of the cell object and the classification is by a pathologist as to whether the cell appears normal or cancerous. The decisions include whether to accept or reject a particular cell for further measurement and processing. The cell object, if selected, can then also be classified into one of several classifications for later statistical analysis. The apparatus further has means which permit the classification and storing of more than one image.

When the apparatus is used for DNA analysis, tissue and cell specimens are applied to a slide which is then stained with a specific stain that combines proportionately with the DNA and essentially renders invisible the remainder of the cell so that the image analysis apparatus can measure the optical density of the DNA which is concentrated in the nucleus of the cell. The stain associates with the DNA to provide a detailed nuclear structure and pattern which may be visually observed and interpreted by the pathologist using the apparatus for classification. The amount of DNA in the malignant cells is substantially greater than that for normal cells because the malignant cells are usually dividing and replicating rapidly or the malignant cells have abnormal numbers of chromosomes or have defective chromosomes.

The Bacus apparatus can not only detect minute alterations in the nucleus by providing a real and accurate measurement of the DNA mass in picograms but also can measure and quantify the amount of DNA and relate it to stored statistical analyses to aid in diagnosis. More specifically, the invention allows an iterative analysis of specimen population cells and provides a histogram or other statistical display of the population distribution of the cells with respect to their DNA content and with respect to a standard DNA for normal cells so that subtle shifts in population distribution can be readily understood. To this end cell nuclei images are not only acquired and stored but the data therefrom can be integrated with other statistical data to provide multivariable analysis, discrimination of cells, histograms, and scattergrams of cells or cell populations.

While the methods and apparatus described above are extremely advantageous and advance the art of aneuploidy analysis by image processing, they are not as sensitive as they could be. With the progress in measuring the quantity and distribution of DNA in a cellular population, there has come the need to further refine and sensitize that analysis and characterization process. One area in which sensitivity of the above described process can be improved is in the operator classification of cell types.

The previous apparatus of Bacus relies mainly on the pathologist or operator to make a subjective judgement concerning the classification of cell types, and whether they are to be classified at all. This is a principal advantage of the apparatus where the expertise of the pathologist in discerning cell types is automated and measurement of specified parameters of the chosen cells is accurately made. However, it has been learned that different cell types which are really quite different structurally appear morphologically similar under the microscope.

This is particularly true when the nuclear DNA has been enhanced by Feulgen staining. Such nuclear staining is for the purpose of enhancing the optical characteristics of the nuclei of the cells which contain the DNA, but that necessarily de-emphasizes the visual characteristics of the cytoplasm in the rest of the cell outside of the nucleus. The result is to allow easier image analysis and precise measurement of the DNA of the nuclear material, but at the same time this enhancement causes the loss of the visual morphological characteristics of the cytoplasm which a pathologist might use to distinguish one type of cell from another. Additionally, there are different cell types, which it is advantageous to classify separately, but which provide no or only faint visual clues as to their differences.

Thus, there is the need to alert a pathologist classifying the cell populations for DNA analysis with the Bacus instrument about the different cell types, whether by optical enhancement or otherwise. A more definitive mechanism would be the use of some demonstrable marker on the cells themselves by which the pathologist can objectively separate the various cell types. There are known in the art many optical enhancement or marking techniques for cell populations, including those described in the above referenced Bacus applications. For example, since the advent of monoclonal antibody production, numerous antibodies have been developed which are specific for cellular components, either in the cytoplasm, nucleus or on the cell membrane. Some have already been used to type cells in pathology to assist in the definition of the cell of origin of a number of tumors where subjective morphology is equivocal.

Among the most notable of these antibodies are antibodies to Leukocyte Common Antigens, which identify inflammatory cells, and antibodies to a family of cytoplasmic structural proteins called cytokeratins which identify cells arising from epithelial structures. Other antibodies to cytoplasmic components such as intermediate filaments can be utilized to identify cells which provide structural support, the so called stromal cells. In addition, numerous antibodies exist which are more specifically related to individual tumor types.

However, further optical enhancement of the cytoplasm for different types of cells is problematic in view of the current DNA staining technique. There are many difficulties, the least of which is that an optical enhancement factor for the cytoplasm should be compatible with the present imaging techniques using computer analysis of optical density and be required to provide such compatibility without impairing the sensitivity of the imaging techniques for the present nuclear staining. Chemical compatibility with the present Feulgen staining technique also presents a major hurdle. Optical enhancement of the cytoplasm after Feulgen staining of the DNA is substantially unavailable because the Feulgen process is destructive of the cell cytoplasm and changes the way it appears normally. However, prior optical enhancement of the cytoplasm is equally as difficult because the Feulgen staining process is caustic with the use of highly acidic reagents which can easily destroy other optical enhancement factors. Moreover, if done prior to Feulgen staining, the optical enhancement process of the cytoplasm cannot affect the nuclear material in a manner such that the result of the subsequent Feulgen staining will be changed.

SUMMARY OF THE INVENTION

The invention provides methods and apparatus for the measurement of selective features and parameters of cells in a population by the optical identification of their type. More specifically, the invention measures the DNA content of selected cells of a subpopulation which is selected from a larger population based on optically marking certain cells in the population.

In a preferred embodiment the optical marking of the cell types is effected by binding an optical enhancement factor, such as a chromogen, to a specific protein in the cytoplasm of a cell in order to type a cell. Particularly, a monoclonal antibody specific to the cytoplasmic protein binds to the protein site and is magnified by an enzyme development technique. After certain types of cells in the population have been tagged with a protein specific optical enhancement, a Feulgen staining process is used to stain the nuclear DNA in all of the cells. An imaging apparatus is then used for the computerized image analysis of the cell population. The apparatus provides means for displaying on a video monitor an image of the cell population from a field of a microscope slide. The image is further digitized and separated into two separate images where in the first the DNA stained areas are visible and in the second the optically enhanced cytoplasm areas are visible. The two image areas are combined and those cells which contain optically enhanced cytoplasm areas are marked so that the operator can visualize those specific cells.

From the digitized DNA areas, the imaging apparatus identifies each possible cell object automatically by a pattern recognition technique. An interactive program allows a pathologist to point on the video monitor to each identified object or cell in succession to make decisions for classification and measurements concerning each. The marked cells can be specifically excluded from a subpopulation by the classification process or specifically included. They may further be identified as to DNA content in a separate classification.

By combining the marking or identification of certain types of cells by an immunohistochemical technique with DNA Feulgen staining, the ability to perform DNA content analysis with a greater degree of accuracy and sensitivity is enhanced. This greater sensitivity provides at least two more avenues of diagnostic and prognostic utility for human tumors. In one method, the immunologic marking can be used to mark which of the cells of a particular population are not derived from the tumor, leaving the remaining cells which are not marked immunologically to be analyzed for DNA content. This method is advantageous where a moderate number of inflammatory cells are present in a tumor. Thus, using an antibody to leukocyte common antigen, the immunological marking can identify these inflammatory cells so they can be excluded from the DNA assay. Alternatively, when the tumor cells are relatively rare and non-tumor cells make up the majority of the cells available for analysis, using immunohistochemical marking which specifically identify tumor cells provides a much easier and more sensitive determination of DNA mass for a cell population. In this case, antibodies to cytokeratin are utilized to identify epithelial derived tumors such as carcinomas. The analysis will then be focused on these cell types while discarding cells negative for cytokeratin as being inflammatory or support cells.

One specific embodiment of the invention includes staining of the cell population with an alkaline phosphatase technique utilizing a monoclonal antibody against a specific cytoplasmic antigen. The resulting stain is substantially specific to the cytoplasm and does not stain the nucleus of the cells. A Feulgen staining process using Thionin is then performed to stain the DNA in the nucleus of each cell. The alkaline phosphatase staining method is used because of its compatibility with the Feulgen staining technique. The alkaline phosphatase staining is specific to the cytoplasmic antigen binding the chosen monoclonal antibody and does not harm the nuclear material so that it may receive the Feulgen stain in a subsequent step. The alkaline phosphatase staining is accomplished first before the destruction of the cytoplasm by the Feulgen staining technique. The chromogen chosen for the staining technique is a fast red dye which is advantageous for two reasons. In the first instance the fast red dye which is precipitated is not susceptible to being washed out by the Feulgen stain process and thus will remain for the optical visualization. The second reason is that the chromogen provides excellent optical separation from the blue Thionin dye used in the Feulgen staining process.

Accordingly, a general object of the invention is to provide a new and improved method and apparatus for analyzing cells or other biological materials by using image analysis techniques.

Another object of the invention is to provide new and improved methods and apparatus for making a quantitative ploidy analysis of cells using image pattern recognition equipment.

These and other objects, features, and aspects of the invention will become apparent upon reading the following detailed description when taken in conjunction with the appended drawings wherein:

DETAILED DESCRIPTION OF THE PREFERRED EMBODIMENTS

Figure 1:
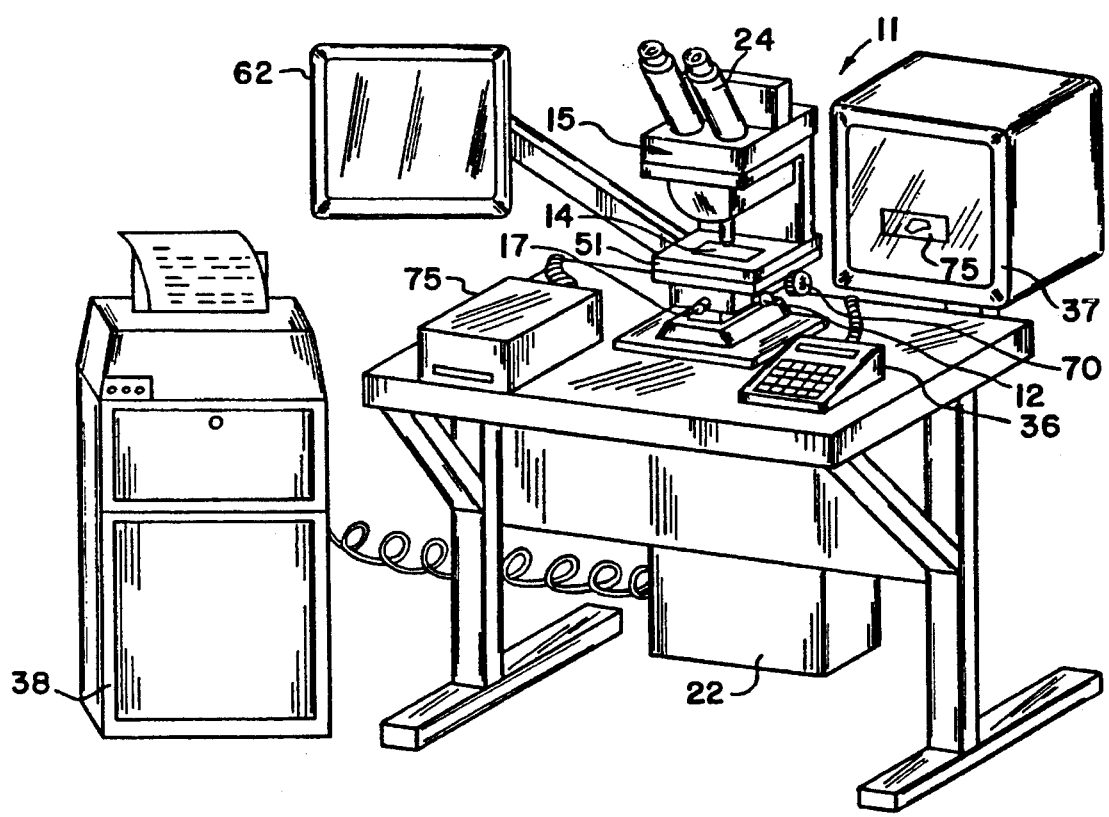
FIG. 1 is a pictorial representation of an image analysis system constructed in accordance with the invention.
Figure 1A:
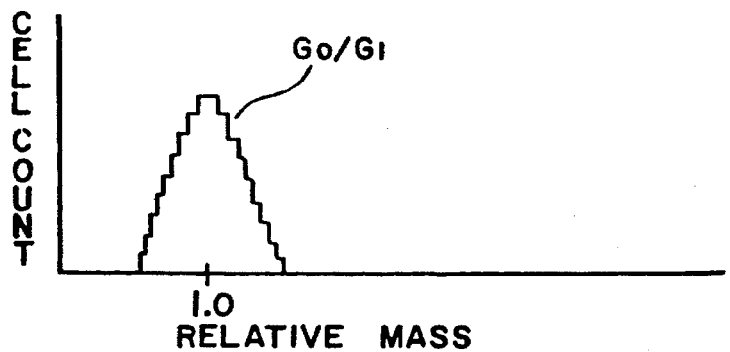
FIGS. 1A–1D illustrate different histograms for aneuploidy analysis.
Figure 1B:
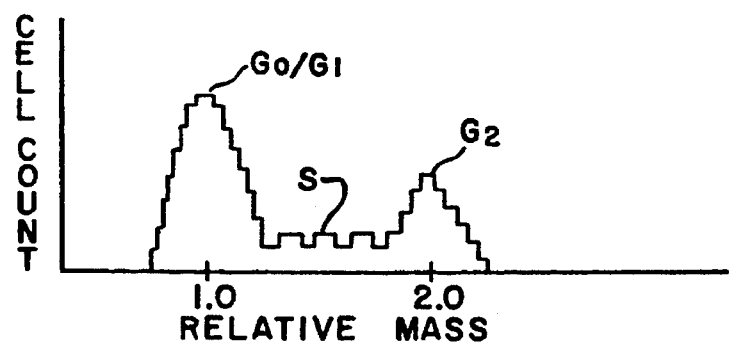
Figure 1C:
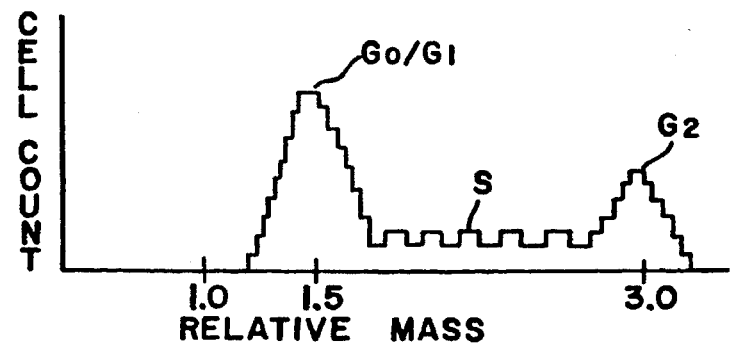
Figure 1D:
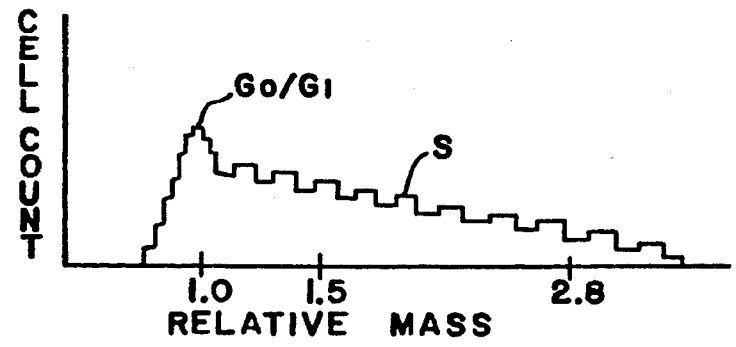
Figure 2:
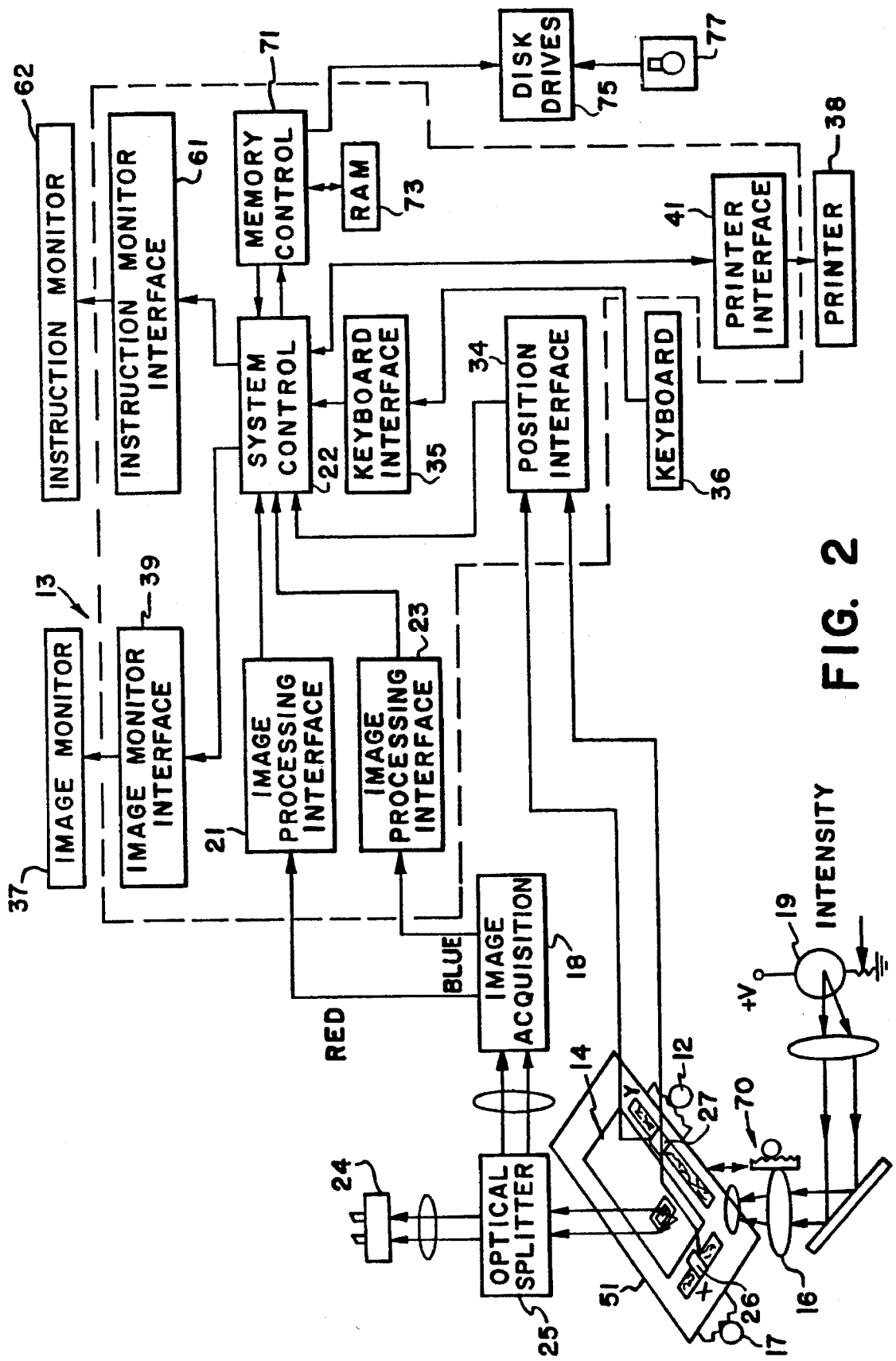
FIG. 2 is a functional block diagram of the image analysis system illustrated in FIG. 1 which is adapted to perform the methods for the quantitation of nuclear DNA in accordance with the invention.

The apparatus illustrated in FIGS. 1 and 2 and the methods described herein can be used to develop histograms, and other statistical data, of cell populations for the diagnosis and prognosis of malignancies and other diseases. Specifically, the quantity and distribution of nuclear DNA in separate or combined classifications of cell populations is available. To illustrate the utility of such statistical analyses reference is directed to FIGS. 1A–1D.

Referring now to FIG. 1A there is shown a normal ploidy histogram having a typical cell number versus mass distribution for healthy, non-dividing cells. The number of cells is provided on the ordinate axis and their nuclear DNA mass on the abscissa. If the cell population shown in the figure is not dividing, the DNA content should be peaked around a normal peak G0/G1 which is the diploid amount, 7.18 picograms/cell. This relative mass of DNA is labelled as 1.0 to normalize the abscissa of the histogram. FIG. 1B also shows a normal cell population which is dividing, such that there is a significant G0/G1 peak at 1.0 and a second peak G2 at 2.0. The peak at 2.0 is normal because some of the cells are in division and have double the normal diploid amount of DNA. The saddle S between the two peaks is relatively low and does not indicate any malignancy.

Comparing the histogram in FIG. 1C with the first two, it is seen that this cell population is skewed from normal by having a higher first peak around 1.5 and a second peak around 3.0. Further, the saddle S is more pronounced and can be rough in cell count. This histogram may show a malignancy because of the abnormally high DNA content for many of the cells. This high DNA content is likely indicative of the increased ploidy amount of malignant cells which are rapidly dividing.

Likewise, in FIG. 1D it is shown that the G0/G1 peak occurs at 1.0 with a normal diploid amount of DNA but has a relatively large trailing saddle from 1.0 to 2.8. A normal G2 second peak is not noted and is indicative of an abnormal cell population. The shape of the histogram is likely due to abnormal DNA amounts in cells and clones of cells indicative of malignancy. Therefore, from the shapes and changes in cell distribution histograms, diagnostic and prognostic information can be obtained.

DNA analysis of human cells has been shown to have both diagnostic and prognostic utility for human tumors. As with any test, its usefulness is dependent on both the accuracy and sensitivity of the technique employed for the analysis. If a tumor specimen were composed only of the tumor cells, the accuracy and sensitivity of the illustrated technique would be a function of the DNA staining and the accuracy of the measuring instrument. However, tumors are most commonly composed of a mixture of cell types. In addition to the tumor cells one finds the normal tissue from which the tumor arose, supportive and structural elements and a variety of inflammatory cells and cells which are part of the repair and defense process of the host. These cells vary in amount from tumor to tumor and may indeed numerically overshadow the tumor cells in many cases.

If non-tumor cells are included in the histograms of the DNA analysis illustrated, several errors can occur:

1. An insufficient number of tumor cells may be identified resulting in a tumor inappropriately being assigned a normal DNA content;

2. In tumors with a normal DNA content, the normal cells will exaggerate the peak on the histogram where the resting tumor cells appear and artifactually lower the percentages of proliferating tumor cells;

3. If the non-tumor cells themselves are proliferating, they will give an artifactual elevation to the assessment of proliferating activity in the tumor.

Thus, an improvement to the DNA analysis could be made with a mechanism to appropriately eliminate irrelevant cells. Among the potential mechanisms are to attempt to distinguish tumor cells from non-tumor cells by cell size and shape characteristics, either quantitatively or by subjective morphologic assessment by a pathologist. The quantitative method is not useful in that tumor cells themselves can vary significantly in size and shape and there is substantial overlap between these parameters in tumor cells and those seen in the non-tumor type cells. The subjective morphologic method is more useful in that it takes into account multiple diagnostic criteria. The present apparatus takes advantage of this by allowing the pathologist to use his subjective skills to separate the tumor cells from the non-tumor cells for DNA analysis. One problem is that the pathologist traditionally uses characteristics of both the nucleus and the cytoplasm to make these subjective judgments. However, when dealing with the previously disclosed method of analysis, only the nucleus is stained making any morphologic assessment more difficult. The invention solves this problem by the optical enhancement or the marking of selected cells, which exhibit a certain characteristic or type to identify them immediately.

In the implementation shown, the system is a computerized image analysis system designed to measure a number of cell object features and parameters from their image on a typical glass slide. The instrument includes a sophisticated digital image processing system controlled by software to perform quantitative analysis on individual cells for nuclear DNA content by Feulgen staining as well as measurement of other nuclear features. The imaging system couples the ability of a pathologist to identify and classify cells to be studied with the capability of computer enhanced, high resolution digital video image processing to quantify optical and stain density accurately. Further, the system optically marks certain types of cells such that the pathologist in making his classifications can include or exclude them from the study to improve the sensitivity of the process.

In general, a pathologist first prepares a needle aspirate preparation of fresh tissue. The sample is first stained with a alkaline phosphatase technique using a monoclonal antibody specific against an antigen in the cellular cytoplasm. The nuclear DNA in the sample is then stained by the Feulgen technique using Thionin as the dye or optical enhancement factor. After fixation and staining, the preparation is ready for analysis.

The operator has the option of classifying the cells morphologically into any one of six categories or rejecting inappropriate cells or debris. The cell data are processed by a system control and the cellular elements are characterized by a quantitative DNA analysis for each cell class. The information when compared with either a standard cell calibration or published data allows a pathologist to accurately quantify and classify abnormalities that might ordinarily be described only verbally from the image.

The addition of quantitative data enables pathologists to perform their work in a more standardized and reproducible manner. The system is of value in classifying lesions that may be malignant and in providing prognostic information for known malignancies based on DNA content. The image identification system is more advantageous than common flow cytometry methods of evaluating DNA content. Flow cytometry permits an operator to classify neoplastic cells based only on cell markers. The pathologist, however, never sees the cells that the instrument has examined. In addition, the cell preparation must be used in a short time frame and is consumed in the course of the study. Although a permanent section of a tumor under study may be examined at the same time, there is no guarantee that the same cells are examined in both areas. Also the quantity of tumor available may not be large enough to permit a flow cytometric examination.

In the invention, the quantitative DNA analysis is performed rapidly for the measurement of DNA and ploidy distribution pattern in a cell population under study. The pathologist advantageously selects the cells which are to be used in the population measurements. The measurement of DNA content is useful and believed to be relevant in diagnosing and determining prognosis for a variety of tumors that involve the breast, colorectum, and prostate. The system takes advantage of the skill of the pathologist and the selected cell marking to visually identify and classify abnormal cells, and then uses the computer aided imaging analysis to analyze quantitatively those particular cells selected for the parameters desired. Such instrument advantageously extends and augments the recognition and diagnostic skills of the pathologist.

With reference to FIGS. 1 and 2 of the drawings, the invention is embodied as an apparatus 11 (FIG. 1) which functionally operates as a digital image analysis and processing system 13 (FIG. 2). The apparatus 11 comprises a high resolution microscope 15 with which an operator can view magnified specimens on a support, in a preferred embodiment a glass slide 14. The microscope 15 includes adjustment or positioning means 70 for focusing its optics 16 on the slide 14 and a platform 51 movable incrementally in X and Y directions via positioning means 12 and 17 in order to view different areas thereof. Positioning means 12, 17 and 70 are the form of mechanical adjustment verniers which are conventional for instrument quality microscopes.

The specimens in the field under study are further viewable by the imaging system 13 via image acquisition apparatus 18 (FIG. 2). The apparatus 18 receives the light intensities of the image of the field and converts them into two analog signals (Red, Blue) which can be sampled and processed by the image analysis system 13. The image analysis system 13 is controlled by a system control 22 in the form of a digital processor such as a personal computer.

An operator, such as a pathologist or laboratory technician, can interactively communicate with the system control 22 via a keyboard 36, and interacts further with the system to quantitate nuclear DNA and classify cell objects by the viewing of two displays or monitors. A first display, image monitor 37, is a conventional RGB video monitor which displays through the system control 22 and the image acquisition apparatus 18, the same image field as seen through the microscope 15. A second display, instruction monitor 62, is another conventional RGB video monitor and is used to provide the operator with interactive prompts, messages, information, and instruction screens from a system program executed by the system control 22.

The keyboard 36 is preferably a conventional AT type keyboard which has on the left-hand side a plurality of function keys F1–F10, in the middle a plurality of alphanumeric keys including the special keys of ENTER, SHIFT, CONTROL, and ALTERNATE, and on the right-hand side cursor control keys including up, down, left and right arrow keys, a numeric keypad, a numeric lock key, and an escape key. A keyboard interface 35 translates the keystrokes of the operator into numerical codes recognized by the system control 22 for specific key indications. A printer 38 is provided for producing reliable hard copy output of the statistical data and reports produced by the apparatus 11.

A functional schematic of the apparatus 11 is illustrated in FIG. 2 as image analysis and processing system 13. The image processing system 13 is used to analyze a plurality of specimen cell objects on the support or glass slide 14 of the microscope 15. Suitable high resolution microscope optics 16 receive light from a variable intensity source 19 and transmit the light through the slide 14.

Because the source 19 transmits light through the cell objects on slide 14, the optical density of each pixel of the image will convert the light into a different intensity depending upon its percentage of transmission. Areas with no cell objects in them will appear relatively light or intense and areas having nontransmissive objects will appear darker. In general, unmodified cell objects are relatively transparent and their features difficult to distinguish. Staining the cell objects allows an optical enhancement of the features stained so they will appear darker than other features and their background.

The optical image of each of the cell objects on the slide 14 passes through an optical image splitter 25. On one side of the splitter 25, the image acquisition apparatus 18, or other detector, converts the optical images point by point into two scanned electronic signals (Red, Blue) representing a monochromatic representation of the optical intensity of each point in the image on the other side of the splitter 25, a true color image of the field is provided to the operator by viewing optics 24.

Figure 3:
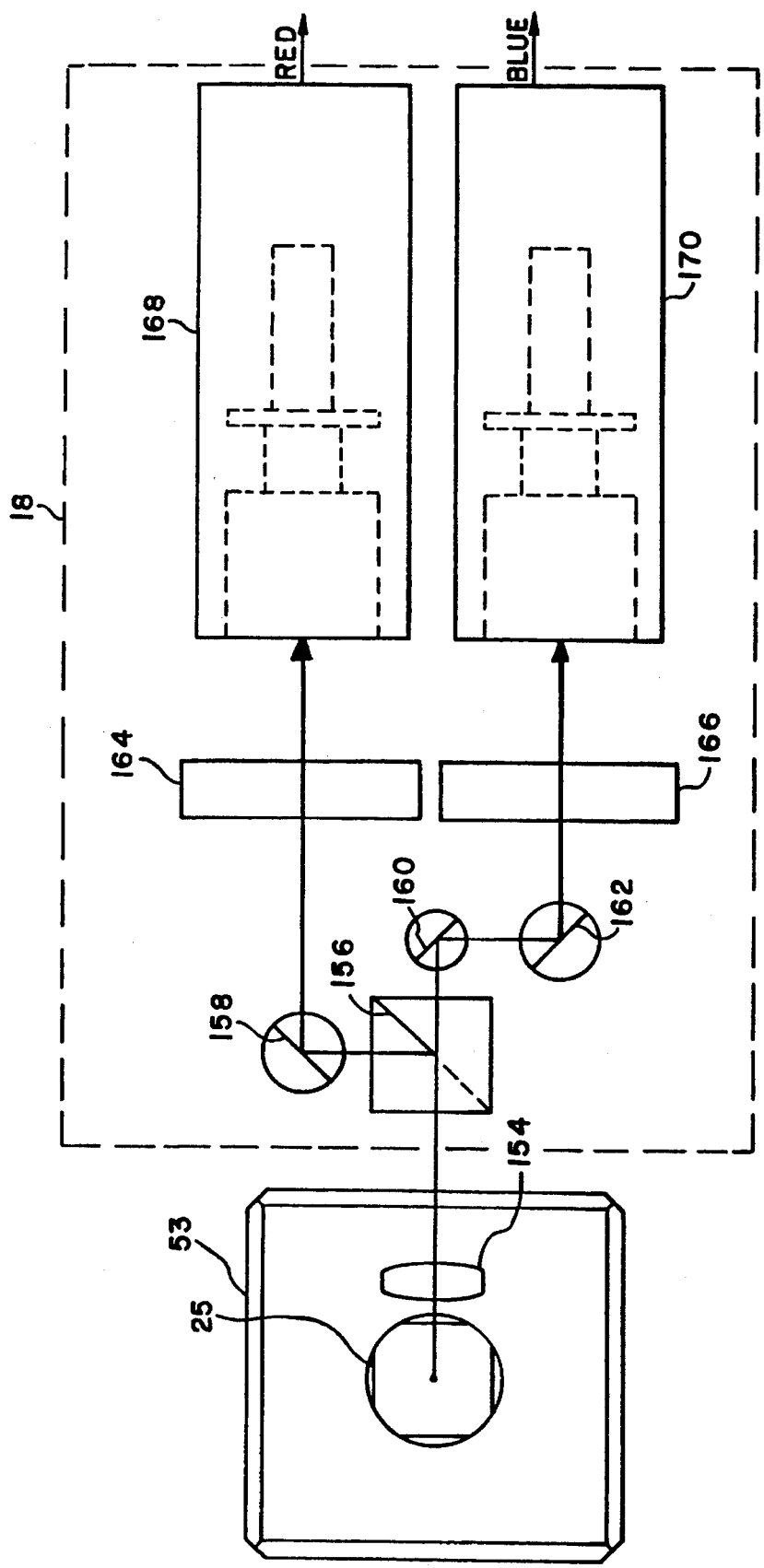
FIG. 3 is a schematic block diagram of the image acquisition apparatus illustrated in FIG. 2.

FIG. 3 illustrates the optical filtering and splitting of the image performed by the image acquisition apparatus 18. The focused image formed by the light intensities is transmitted substantially vertically through the slide 14 and enters the beam splitter 25 mounted in a holder 53. The first true color image passes vertically therethrough. A second true color image is further transmitted by the beam splitter 25 perpendicular to the vertical path through the focusing lens 154 to image acquisition apparatus 18. The image acquisition apparatus 18 comprises a plurality of optical elements including a second image splitter 156, mirrors 158, 160 and 162, and two monochromatic optical filters 164 and 166. The image acquisition apparatus 18 further includes dual video cameras 168 and 170 which each receive a portion of the split image. After the second true color image is split from the microscope optics, it passes into the second beam splitter 156 where along one path the image is reflected by mirror 158 through filter 164 and imaged by camera 168. Along a second path, the image is reflected from mirror 160, to mirror 162, and then through a second filter 166 to be imaged by camera 170. The filters 164 and 166 are narrow bandpass filters substantially blocking all light frequencies outside their pass band. The images from cameras 168 and 170 are therefor essentially monochromatic images of the field under study on the slide 14. The first filter element 164 comprises a red filter which passes on light of a narrow bandwidth of wavelengths near 620±10 nanometers. The second filter element 156 is a blue filter which passes light of a narrow bandwidth of wavelengths near 480±10 nanometers.

Each television camera 168, 170 converts the monochromatic optical images point by point into a scanned electronic signal representing the optical intensity of points in the image. The output of the cameras 168 and 170 which is formatted as a standard National Television System Committee "NTSC" analog video signal is applied to an analog to digital converter of a pair of image processing interfaces 21, 23. Each image processing interface 21, 23 samples the analog signal from each camera 168, 170, respectively, and converts the image signal to a digitized signal which is received and stored by the system control 22. Because of the continuous scanning, a real time image of the area that the optics 16 are focused on is provided by the image display 37. With the dual camera arrangement either a red color image or blue color image is available simultaneously to the system control 22. In general, each monochromatic digital image is stored as a 512×512 array of pixels where each pixel has a measured light intensity of 0–255 (8 bits).

Because the viewing optics 24 of the microscope 15 are located on the other side of the image splitter 25, this parfocal arrangement allows the same image seen in the viewing optics 24 to be displayed on the image display 37. This feature allows the positioning of the platform 51 by the manual X, Y adjustment of positioning means 12 and 17 until the operator views a field of interest on the slide 14. At that time, the computer enhanced digitized image of the selected field is displayed on the image display 37 for further analysis. An X position sensor 26 and a Y position sensor 27 generate position signals to a position interface 34 which digitizes these signals to provide the apparatus 11 with an accurate coordinate representation of the field in view.

Both of the displays 37 and 62 are controlled by the system control 22 through standard video monitor interface circuitry 39 and 61, respectively. Similarly, the keyboard 36 and the printer 38 communicate with the system control 22 through conventional interface circuits 35 and 41, respectively. In addition, the system control 22 controls a random access memory 73 and other bulk memory storage in the form of either floppy and hard disk drives 75 through a memory control interface 71.

All of the interface circuits 21, 23, 34, 35, 39, 41, 61, and 71 can be selectively embodied on printed circuit boards which are mounted in the backplane or card connector of a conventional personal computer forming the system control 22. Preferably, the personal computer can be one manufactured by the IBM Corporation having a model designation AT, or those compatible therewith. Such system control 22 can be run under a disk operating system such as PC DOS, version 3.1 or later. The system software for the image analysis is called as an application program from the disk drive 75, and could for example, be supplied on a floppy disk 77. The system software is read from disk 77 and loaded into Random Access Memory "RAM" 73. After loading, program control is transferred to the system software from the operating system to regulate the various hardware elements of apparatus 11 previously set forth in a known manner.

The image analysis system 13 operates under an interactive program control by providing a number of instruction screens or images on the instruction monitor 62 to assist the operator in the quantitation of nuclear DNA found in one or several cell subpopulations displayed on image monitor 37. Through interactive responses by the operator and menu selections on different instruction screens, the basic system functions of the image analysis are performed.

Figure 4:
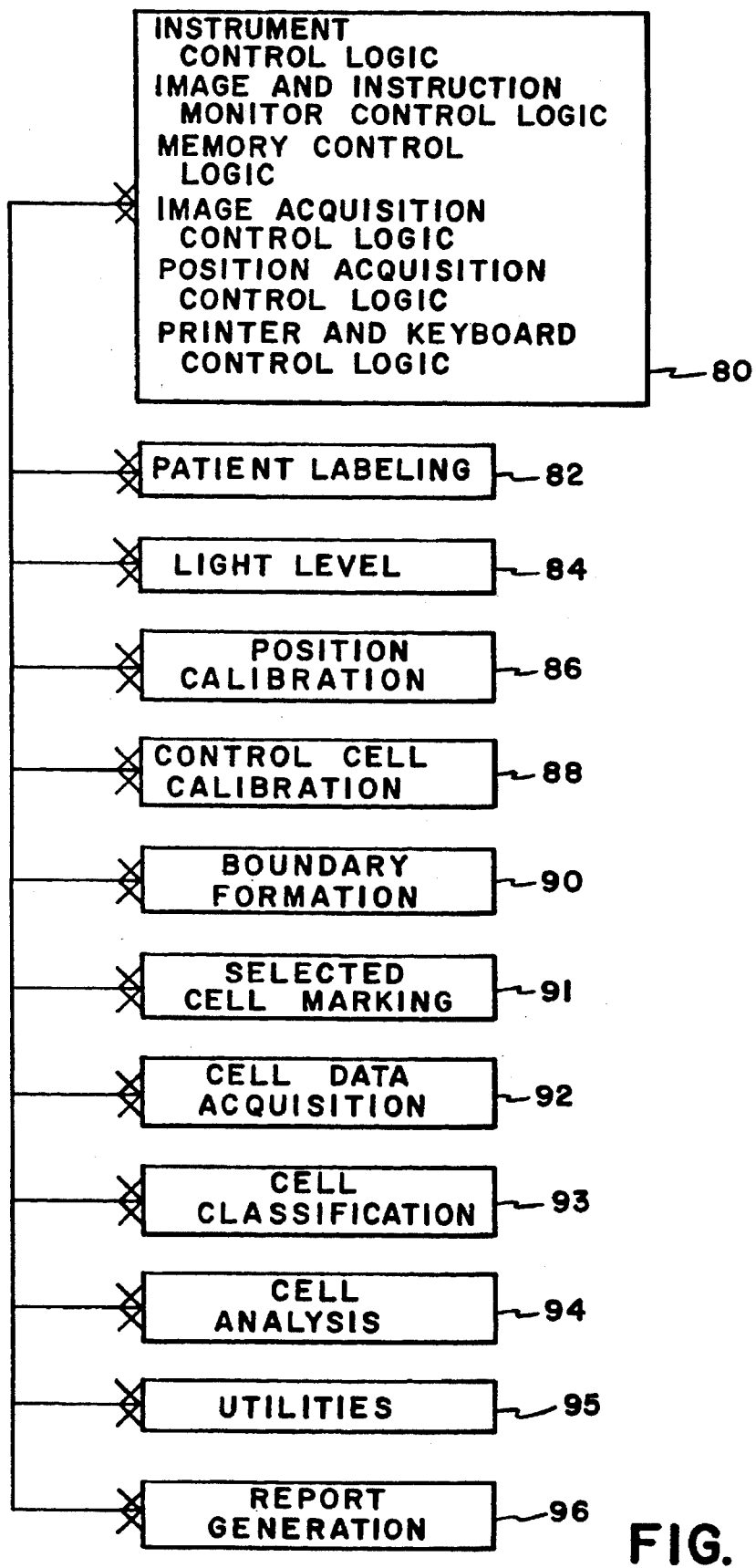
FIG. 4 is a functional system diagram illustrating the major operations of the system control illustrated in FIG. 2.

The system functions are more fully illustrated in FIG. 4 where software control logic functions for the hardware in block 80 are shown communicating with software analysis and measuring functions of the system software in blocks 82–96. Software is included in the system to perform an initialization and an interfacing of the operating system functions and overall control of the apparatus 11 by instrument control logic. A screen handler for the instruction screens and the video display of the digital images of the specimen is performed for both of the monitors 37 and 62 by image and instruction monitor control logic. The memory and disk storage functions are handled in the software by memory control logic. Input and output for the interactive responses and reports are handled by the printer and keyboard control logic. Further, data from the cameras 168, 170 and from the position sensors 26, 27 are handled by image acquisition control logic and position acquisition control logic, respectively.

The control logic of the software forms an operating shell which is used by the analysis and measuring functions in blocks 82–96 to control the hardware of apparatus 11 to perform the particular function needed. The system provides a patient labeling function 82 to identify the particular tissue samples which are under study. Light calibration and position calibration functions 84 and 86, respectively, are used to determine a correct reference optical density for a particular field and the location of that particular field with respect to a coordinate origin. A control cell calibration function 88 provides a datum for the compensation of different background stainings and DNA index calibration. A boundary formation function 90 allows the operator to choose a reference level against which the grey scale values of an image are compared for either the red image or the blue image. A selected cell marking function 91 provides for the marking of those cells identified by the cytoplasm optical enhancement in the acquired data function. The cell data acquisition function 92 provides for the storage of the grey scale values of the measurements on a specimen image. A cell classification function 93 allows the operator to classify the acquired cells, taking into account those marked cells, into different categories, and a cell analysis function provides different statistical analyses of the categorized data. A utilities function 94 provides the needed auxiliary type programs for assisting in the primary functions of the image analysis. A report generation function 96 is used for hardcopy production of analyzed and compiled data from the system on the printer 38.

Figure 5:
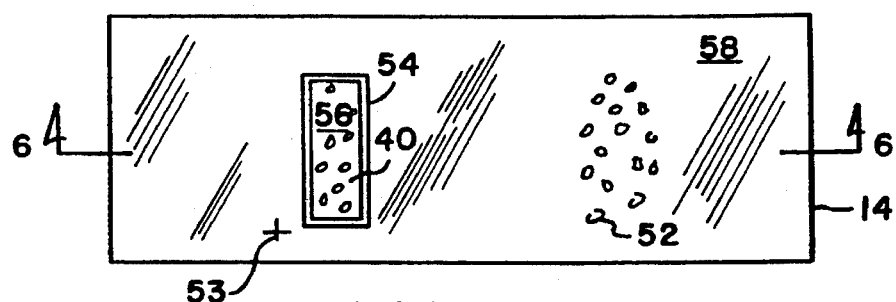
FIGS. 5 and 6 are top perspective and cross-sectional views, respectively, of a slide particularly adapted for use in the image analysis system illustrated in FIG. 1 and having separate areas for calibration cell objects and specimen cell objects.
Figure 6:

The support on which a specimen is viewed preferably is a transparent glass slide 14 as illustrated in FIGS. 5 and 6. Glass slides of a rectangular shape come in standardized sizes such as 1" by 3" and such can be used with the following modifications. The slide 14 is partitioned into two sections where in a first control section 56 are located control cell objects 40. In a second section, specimen section 58, there are located specimen cell objects 52 which are to be measured for their content of DNA. The slide 14 further includes a border 54 around the control section 56 for rapid identification of that section. Further, on some convenient location of the slide 14 is placed an identifying mark 53. The mark 53, illustrated as a cross in FIG. 4, is used as a landmark for identifying the coordinate origin for fields on the slide.

Because the apparatus 11 may be used in various offices such as pathology offices having persons of varying degrees of skill and knowledge about image analysis, the microscope light source 17 may be variously adjusted by different operators such that the background may have a different light intensity not only from machine to machine but also at different times depending on the age and nature of the lamp doing the illumination. When the cell objects are DNA nucleus, the stained nuclei appear darker and have high darker gray levels than the cells which have fewer or no DNA content. The particular light intensity level is desired to be known in an accurate and real manner; and hence, it is important that there be a calibration of the light intensity to eliminate errors which might be introduced if differences in light intensity levels are not accounted for.

A further problem with widespread usage of equipment of the foregoing kind is the Feulgen staining factor by which is meant that the user may be applying either a heavy amount or a light amount of the Thionin stain. This will result in a variation of the gray level being viewed through microscope 15 and by the cameras 168, 170 which is then analyzed as to the particular DNA content. Thus, there is a need that the apparatus 11 be calibrated to eliminate differences because of the staining factor so as to provide a true indication of the actual amount of DNA being analyzed.

In accordance with the present invention, a calibration material 40 is provided on the slide 14 which, when viewed by the operator under a calibration step of the system software, allows the operator to adjust and to calibrate the apparatus prior to the measuring and analyzing of specimen cell objects on the slide 14.

In the illustrated embodiment of the invention there are provided two different materials on the slide 14 with the first being the control cell objects 40 which are stained simultaneously with the staining of the specimen cell objects 12. The simultaneous staining permits the analysis of the control cell objects to be compared to a predetermined stored reference light intensity, gray level, or optical density which the control cell objects 40 have after staining. If the cell objects are stained either too lightly or too heavily, the amount of understaining or overstaining can be quantitatively analyzed and adjusted for as will be described hereinafter.

The control cell objects 40 are, in this illustrated embodiment of the invention, rat liver cells of a known size and shape, and DNA content. The control cell objects 40 may be other types of cells having dark centers or nuclei which stain well, such as chicken blood cells or trout cells. On the other hand, the cell objects 40 may be artifacts printed on the slide to have a cell shape. Furthermore, as above explained, the cell objects 40 may be conventional plastic beads of a predetermined size which will react with a particular fluorescent stain or enzyme stain when treated simultaneously with specimen cell objects such as monoclonal antibodies used in the specimen area 58 of the slide. The reference cell objects will vary from test to test and the present invention is not limited to any particular test or cell objects.

A pathologist will take a slide such as shown in FIGS. 5 and 6 having premounted thereon the control cell objects 40, and add thereto the specimen cell objects 52 which are, in this instance, cells from a needle aspirate of tumor tissue or monolayer of blood cells or other cells, at the area 58 on the slide. The pathologist will then stain or otherwise treat simultaneously the control cell objects 40 and the specimen cell objects 52 for image enhancement.

A kit is provided with the apparatus 11 which contains the slide 14 with the control cell objects 40 thereon, and bottles of reagents which are needed for the dual staining technique. For the alkaline phosphatase staining technique the kit contains bottles of a primary antibody reagent, a biotinylated secondary antibody reagent, an Avidin-Biotin, alkaline phosphatase reagent, and a chromogen substrate (preferably fast red). For the Feulgen staining technique the kit contains bottles of Thionin reagent solution and rinse reagent.

To prepare a slide 14 for analysis, the following process is used. The slide 14 having control cells in section 54 and specimen cells in section 58 is first stained with the alkaline phosphatase technique to optically enhance a specific cytoplasmic antigen. The immunohistochemical staining begins with a nonfixed specimen on slide 14 which is initially cold fixed at 40° C. in acetone for 20 minutes. The slide is then rinsed twice in a phosphate buffered saline solution for five minutes (each rinse) without allowing the slide to dry. The slide 14 is then incubated for 15 minutes at 37° C. in a moist environment with a solution of 2 ml. to which has been added 10 drops of normal horse serum. This step prevents much of the nonspecific binding of the antibody to sites of the cell objects.

After draining the excess of the normal horse serum solution off the slide 14, it is incubated 15 minutes at 37° C. in a moist environment with the primary antibody which binds to he antigen in the cytoplasm of the cell objects.

The slide 14 is again twice rinsed in a phosphate buffered saline solution for 3 minutes (each rinse) without allowing the slide to dry. Next, the slide is incubated for 15 minutes at 37° C. in a moist environment with biotinylated bridging antibody solution. The dilution of the antibody solution being 1:400. The slide is again twice rinsed in a phosphate buffer saline solution for 3 minutes (each rinse).

Thereafter, for development and magnification an Avidin-Biotin, alkaline phosphatase solution is incubated with the slide 14 for 15 minutes at 37° C. in a moist environment. Solutions of A-B complex and alkaline phosphatase solution are available from the Vector Corporation of Burlingame, Calif., as solution A, and solution B of kit number SK-5100. 50 microliters of solution A and 50 microliters of solution B is mixed with 5 milliliters of a 1% Bovine serum albumin/phosphate buffered saline solution to form the development solution.

The slide is again rinsed twice in a phosphate buffered saline solution for 3 minutes (each rinse). A chromogen substrate is then added and reacts with alkaline phosphatase to produce a colored precipitate. Preferably, the substrate is red dye, fast red, from the same kit as above which contains dye solutions 1, 2, and 3. Two drops each of solutions 1, 2, and 3 are added to 5 milliliters of 100 mM Tris with a pH of 8.2. This solution is incubated with the slide for 15 minutes at 37° C. in a moist environment. The final step in the cytoplasm development is to rinse the slide for 1 minute in distilled water.

The slide 14 is then stained with the Feulgen technique using Thionin to optically enhance the nuclear DNA of each cell. The slide 14 is fixed in 10% by volume buffered formalin, adjusted to a pH in the range of from about 7.2 to about 7.5, for 10 minutes at room temperature. The nuclear DNA of the cell objects is then hydrolyzed by treating the slide 14 for about 60 to 75 minutes in 5N hydrochloric acid. The staining process is accomplished on the slide by transferring it to a Thionin solution for about a one hour period. Afterward, the slide 14 is washed in a three state process of rinse solution. The slide is placed in a first stage of rinse solution for about 30 seconds, transferred to a second stage of rinse solution for about 5 minutes, and then permitted to stand in a third stage of rinse solution for about 10 minutes. The slide is subsequently washed for about 5 minutes in running distilled water, and thereafter washed with acid alcohol (0.37% hydrochloric acid, 70% ethanol) for 5 minutes. The slide 14 is then dehydrated in absolute ethanol for about 5 minutes to prepare it for coverslipping. Finally, the slide is cleared in xylene for about 5 minutes before being mounted with a synthetic resin and coverslip.

Figure 7:
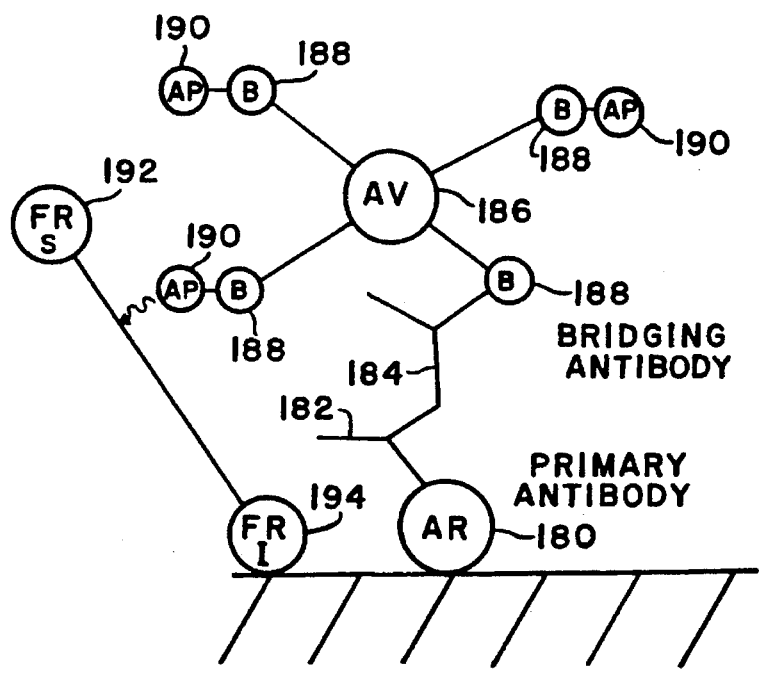
FIG. 7 is a pictorial view at the microscopic level of the binding effects of a monoclonal antibody.

In FIG. 7 there is shown a representative drawing of the marking and amplification of a particular antigen site 180 labelled AR. The site is an antigenic against a primary antibody 182 that binds thereto. In the preferred embodiment, a bridging antibody 184 against the primary antibody is used to bind to the primary antibody and has affixed a Biotin molecule 188. To the bound primary and bridging antibodies is added Avidin-Biotin complex including an Avidin molecule and three Biotin molecules 188. These Biotin molecules 188 are conjugated with molecules of alkaline phosphatase AP enzyme 190. The fourth Biotin molecule site is open to binding the complex to the bridging antibody 184. The site, when a dye such as fast red molecules 192 in solution is added to this mixture, the alkaline phosphatase reacts with the dye molecules to produce insoluble fast red molecules 194 which mark the antigen site. While the Avidin-Biotin complex is exemplary and preferred, any number of different marking techniques can be used. Alternatively, a bridging or primary antibody which is anti-alkaline phosphatase can be used, and then amplified by fast red dye in the manner previously described.

A dual filtering method is thereafter applied to distinguish the areas (cytoplasm) stained by the red chromogen and the areas (DNA) stained by the blue Thionin. These images, one by the red filter and the other by the blue filter, are used to separate the DNA stained areas from the cytoplasm areas containing the specific antigen, and to separate both of these areas from other cell or field features.

Figure 8:
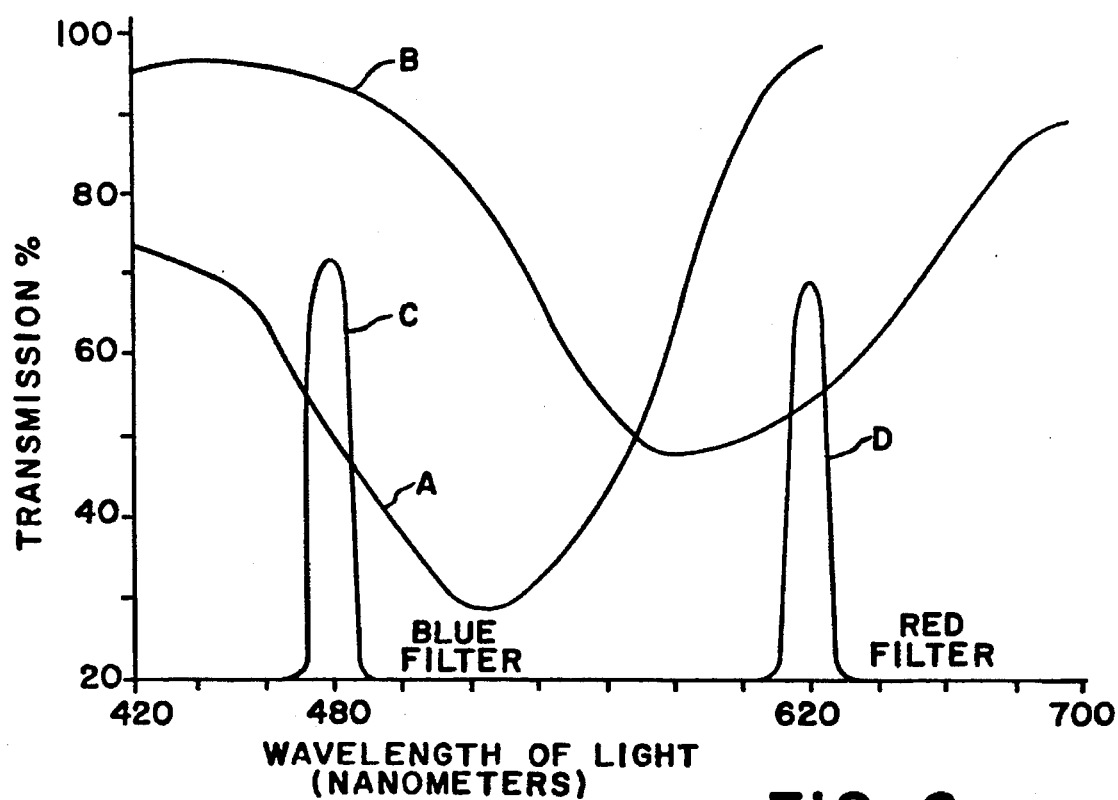
FIG. 8 is a graphical representation of the % of light transmission as a function of light wavelength for the two stains and the two color filters used in accordance with the invention.

The results and desirability of this dual filtering of a stained cell image are more fully illustrated in FIG. 8. The percentage of light transmitted through the nuclei stained with Thionin dye is shown in the curve A as a function of the wavelength of light. The percentage of transmission of light for fast red dye is shown in curve B as a function of the wavelength of light. The bandwidth of wavelengths of light passed by the blue filter is illustrated in band C while the bandwidth of wavelengths of light passed by the red filter is illustrated in band D.

When a true color image of a cell population or specimen is filtered with the blue filter 166, substantially all of the areas stained with the fast red dye will be invisible and substantially all the areas stained with Thionin dye visible. This is because the Thionin curve A has a relatively non-transmissive peak near this wavelength band (480 nms.) while the fast red curve B is relatively transmissive in this band. Thus, in this manner the areas with Feulgen stain can be separated from the cytoplasmic areas. At the other extreme of the graph, the band D of the red filter 164 is positioned at a place where just the opposite occurs. The Thionin curve A is relatively transmissive in this bandwidth while the fast red curve B is relatively nontransmissive. Thus, the cytoplasmic areas containing the fast red dye can be identified without a problem.

Because of the opposite relative differences in light transmission between the two stains in the two filtered bandwidths, the Thionin stained area is enhanced during one filtering relative to other areas of the cell, and the fast red stained areas are enhanced relative to other areas of the cell during the second filtering. While the implementation shows a convenient and advantageous method for discriminating between the two areas having separate staining, it is recognized that there are various other staining or optical enhancement methods and filtering methods which can be used to optically enhance one particular area or feature over another cell area.

The system software for DNA analysis can now determines the mass of the cellular DNA by obtaining the optical density of the specimen cells from the Thionin stain via the instrument 11. In general, the mass of the DNA of a stained cell object can be obtained from its optical density by utilizing the Beer-Lambert Law which is well known in the art of microspectrophotometry. The equation states:

$$M = \frac{\alpha \epsilon OD}{E\lambda}$$

where

M=mass of the object in picograms
$\alpha$=spot size in $\mu m^2$
E$\lambda$=extinction coefficient of the stain at wavelength $\lambda$ in $\mu m^2/pg$.

OD=optical density of each spot (dimensionless)

The instrument uses this law to find the mass distribution of a number of cells or cell objects which can then be analyzed according to a statistical basis, histogram, or other analytical format as will be discussed hereinafter. The spot size $\alpha$ is determined by the number of pixels which are measured by the camera 18. The optical density for each pixel is calibrated by adjusting the light level, focus, and reading a reference optical density from the calibration area on the slide. This calibration allows the conversion of the measured light levels for each pixel into an optical density, a dimensionless quantity.

A calibration for the extinction coefficient is accomplished by measuring the optical density for a plurality of the control cells 40 to determine a peak for the distribution in relative mass units. Because the peak DNA content is known for the control cell distribution, the cells in the measurement field can be measured using the relative OD units and then converted directly into picograms by using the control cell calibration. For example, if the control cells are known to contain pg of DNA (rat liver cells) and a group of calibration cells show a peak distribution of 11,000 relative OD units then a normal group of human cells (with a known DNA content of 7.18 pg.) would exhibit a peak in their distribution at approximately 13,250 relative OD units. Further, any other relative OD unit measurement can be converted directly into picograms by determining and using the extinction coefficient found from the group of calibration cells.

Figure 9:
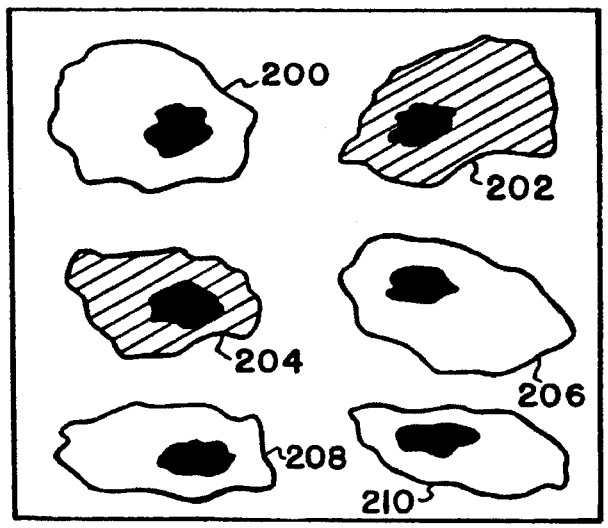
FIGS. 9, 10, and 11 are pictorial representations of images of a cell population showing an unfiltered image, a red filtered image, and a blue filtered image, respectively.
Figure 10:
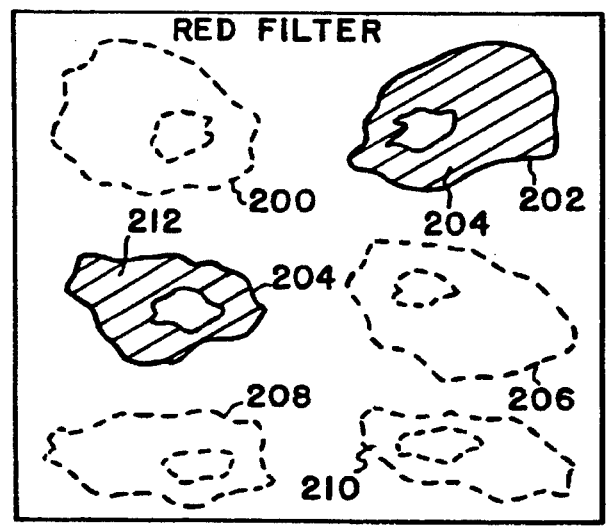
Figure 11:
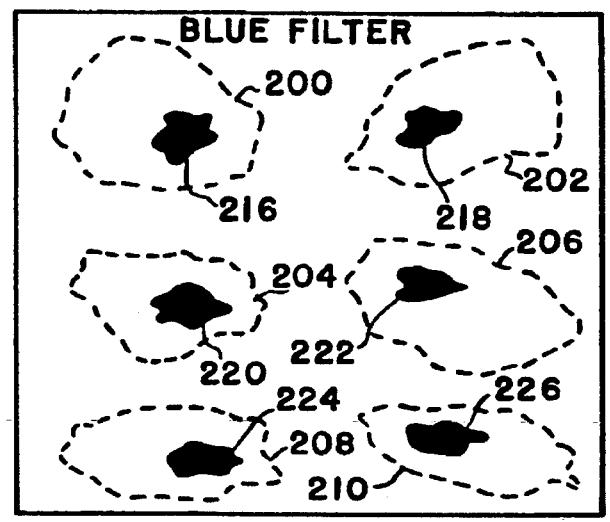
Figure 12:
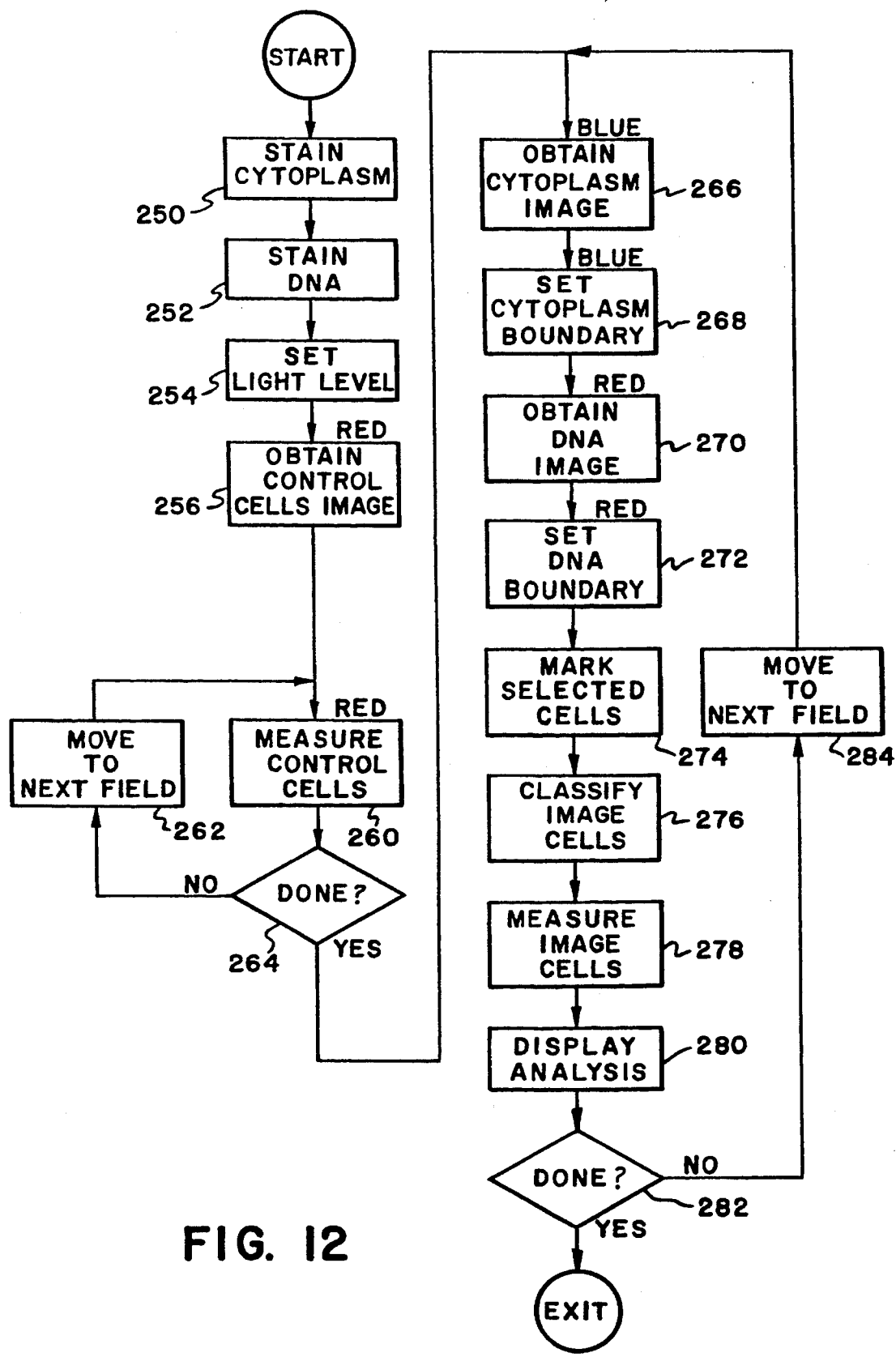
FIG. 12 is a functional flow chart of one preferred method of quantitating DNA for human carcinoma in accordance with the invention.

The method of the invention is combined with this technique as will now be more fully described with respect to FIGS. 9–12. FIGS. 9–11 are pictorial representations of the true color image of a field of a slide 14 (FIG. 9), an image filtered with the red filter (FIG. 10), and an image filtered with the blue filter (FIG. 11). FIG. 12 is a flow chart of the steps in the method to produce quantitation of nuclear DNA.

In FIG. 9 there is illustrated several cells of a subpopulation from one of the fields of the microscope slide 14. The subpopulation contains different types of cells, wherein specific cells 202, 204 have been optically enhanced by the alkaline phosphatase staining. All the cells 200, 202,204, 206, and 210 have had the DNA in their nuclei optically enhanced by Feulgen staining with Thionin dye.

When filtered with the red filter in FIG. 10, only those areas which contain the fast red dye are visible. These are the cytoplasmic areas 212, 214 of cells 202,204 respectively which have been optically enhanced because they contain a specific antigen which binds the monoclonal antibody of the alkaline phosphatase staining. These types of cells 202,204 are different from the cell types 200, 206, 208, and 210, which are invisible in this image. Further, the nuclei of all cells 200, 202, 204, 206, 208, and 210 can be made invisible in the background because of the optical separation of the Thionin dye and fast red dye.

In FIG. 11 there is illustrated the result from the blue filter, where all the nuclei 216, 218, 220, 222, 224, and 226 from the cell population are visible. The image filtered with the blue filter produces an exclusion of those cytoplasmic areas which are not nuclear stained (clear rather than stained), and which are optically different (fast red stained) even if stained.

Figure 13:
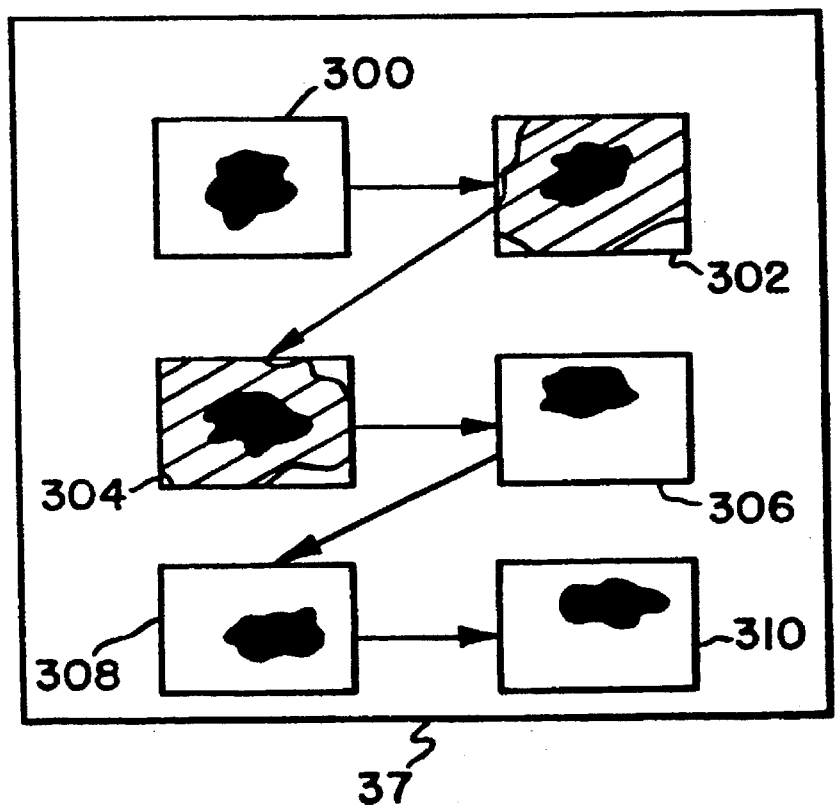
FIG. 13 is a pictorial representation of the image monitor 37 during the selection process, illustrating the marked cells.

The areas stained above the thresholds set for each filtered image can then be combined by overlaying the DNA image on the cytoplasmic image digitally to present on the monitor a clear image of the DNA nuclear areas for typing and analysis where certain cells 202, 204 are marked clearly as to type by an identifying cytoplasmic ring or crescent on the nucleus in FIG. 13. The DNA analysis then proceeds by the interactive classification of each cell in the image displayed on the image monitor 37. The specifically marked cells 202, 204 can be included in any class, excluded from any class, or classified entirely separately from any other class. Further, it is evident that different optical enhancements and filterings will give rise to different typings and increase the sensitivity of the classification process.

The method of measuring and analysis of nuclear DNA using the marking technique of the invention is more fully illustrated in FIG. 12. In a first step, in block 250, a slide 14 containing control cell objects and specimen cell objects is stained with the alkaline phosphatase technique using fast red dye. The monoclonal antibody is specific against a cytoplasmic antigen, for example, Leukocyte Common Antigens or Cytokeratins. The next step in the process is to stain the slide 14 with the Feulgen process using Thionin in block 252. After mounting, the slide 14 is placed on the platform 51 of the instrument 11 and the operator positions the slide 14 such that a clear field is shown on the image monitor. The light level is then set for the instrument in block 254.

The platform is then moved to the control cell area where an image of a subpopulation of the control cells appears on the monitor 37 in block 256. This image is the filtered image (red) showing only the Feulgen staining. The amount of staining to determine the DNA index, such that mass can be determined from optical density, is found by measuring optical density of the control cells in block 260. Normally, more than one field of control cells is measured to obtain an accurate measurement and this step can be repeated by looping through block 264 and block 262. In block 262, the operator moves the platform 51 so that another field of control cells comes into view.

The measurement of the peak of the optical density units is converted into the DNA index and stored. The instrument may now be used to measure and analyze the DNA of specific cells on the specimen section 58 of the slide 14. To this end, the instrument platform 51 is moved to a field where specimen cell objects are visible.

Initially, a cytoplasmic image of the specimen field is obtained using the blue filter in block 266 and its boundary set in block 268. Thereafter, a DNA image of the specimen field is obtained using the red filter in block 270 and its boundary set in block 272. These filtered images are real time images of the field and are being constantly updated by the image acquisition means 18 of the system 11. The apparatus 11 combines the two filtered images in block 274 to mark the selected cells on the image monitor 37 while displaying the DNA nuclear area. The program then proceeds to a classification step in block 276. When in the classification mode the image acquisition and combination (marking) halts and a static image is presented on the image monitor.

The cells in the image on monitor 37 are then classified as to type by an interactive process with an operator where each cell is pointed to by the apparatus, and the operator in response to the identification selects a classification for it using the nuclear morphology and the cytoplasmic markings of the combined image. The classified cells are then measured for DNA content in block 278 and the results of the measurements displayed in block 280. The display can be in various forms and statistical analyses of the different classifications or combinations of classifications.

The measurement step can include more than the cells in one field by looping through block 282 and block 284. The operator moves the platform 51 of the apparatus 11 to another specimen field in block 284 and the marking and imaging steps proceed as previously described. The data accumulated in the measuring step for the new cell population is added to that developed for the previous cell population(s). The display step in block 280 can be delayed until a significant amount of data is accumulated or a display of each iteration provided at the option of the operator. The operator further has the option to bypass setting the cytoplasm boundary and DNA boundary once they have first been set for a specimen image.

The system program for DNA quantitation is, in general, a menu driven program which allows the operator to interactively communicate with the image analysis system 13 to produce the quantitation of nuclear DNA by image analysis. The system program displays a plurality of images or instruction screens on the instruction monitor 62 which include menus from which to select the various functions needed for performing a quantitative nuclear DNA assay. FIG. 17 illustrates the screen architecture of the system and the paths that the system takes between screens. Examples of two of the system screens, the calibrate screen A14 and the analysis screen A16, which appear on the instruction monitor 62 are pictorially illustrated in FIGS. 15 and 16, respectively.

Returning to the reference numerals in FIG. 17, the system program may be run by calling it as an application program of the operating system A10. Selection of the system program by the operating system A10 produces the main screen A12 on the monitor 62. From the main screen A12 the operator can select a calibrate screen A14, an analysis screen A16, or exit back to the operating system A10. While displaying the calibrate screen A14, the instrument can be calibrated to provide the background or reference light settings which will be used in the measurement of the assay. Once the light calibration is complete the operator can select the analysis screen A16 which is used to measure and classify the cell objects of the assay technique.

One of the options in analysis screen A16 is to adjust the blue boundary which assists in forming the nuclear areas. Another of the options is to adjust the red boundary which produces the adjust red boundary screen A20. Once the nuclear and cytoplasmic areas have been bounded by the screens A18, A20, the operator can select the analysis screen A16 to actually do cell measurement, classification and to generate reports. Exits from the adjust blue boundary screen A18 and from the adjust red boundary screen A20 are to the analysis screen A16, which can then exit back to the main screen A12.

In this manner an advantageous screen architecture is formed which can be easily used and understood by the operator. This screen structure facilitates the interactive measurement of the nuclear DNA of the particular cell subpopulation under study. The instruction screens provide an interactive use of the digital imaging system which combines the power of the system software and hardware with the judgment and knowledge of the operator. The screen structure automates the assay task of nuclear DNA quantitation while still permitting the operator to selectively choose the input data and control the process to a considerable degree.

Each screen A12–A20 contains a menu of the functions permitted for use while that particular screen is being displayed on the instruction monitor 62. The function that the system is to currently execute in a particular menu is chosen by the operator with a cursor movement method using the standard cursor control keys of keyboard 36. While a particular screen is being shown on the monitor, the cursor movement keys are operable to position the cursor next to a particular function listed on the menu of that screen. While the cursor highlights the function by its position, the operator may select the function for execution by pressing the enter key.

Figure 18:
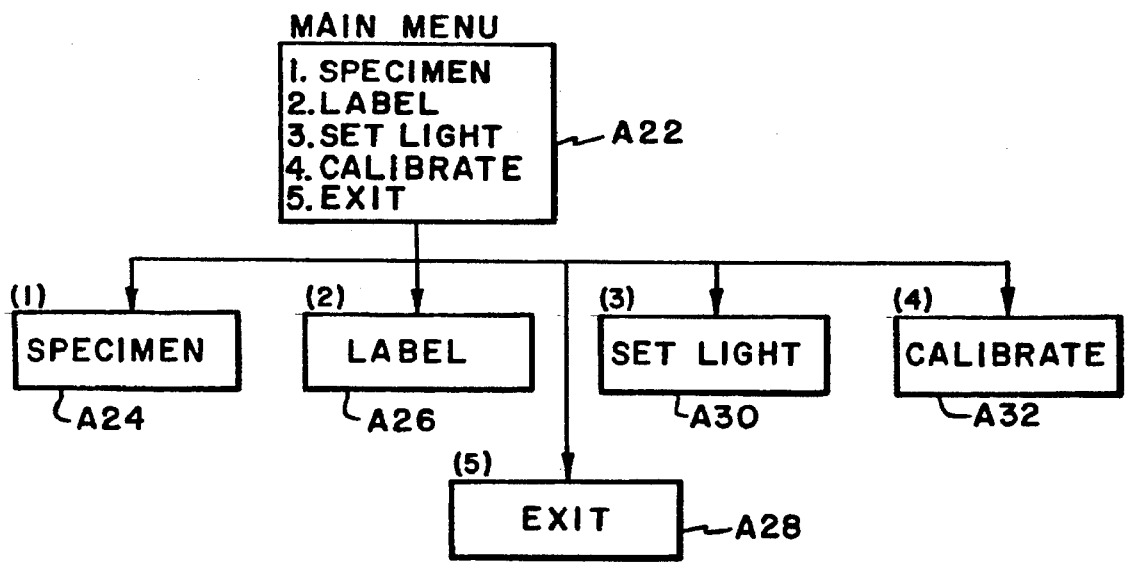
FIG. 18 is a functional flow chart of the main menu of the main screen illustrated in FIG. 17.

The main screen 12 displays the main menu A22 illustrated in FIG. 18. The main menu A22 provides five choices which include 1) a specimen function A24, 2) a label function A26, 3) a set light function A30, 4) a calibrate function A32, and 5) an exit function A28.

Figure 19:
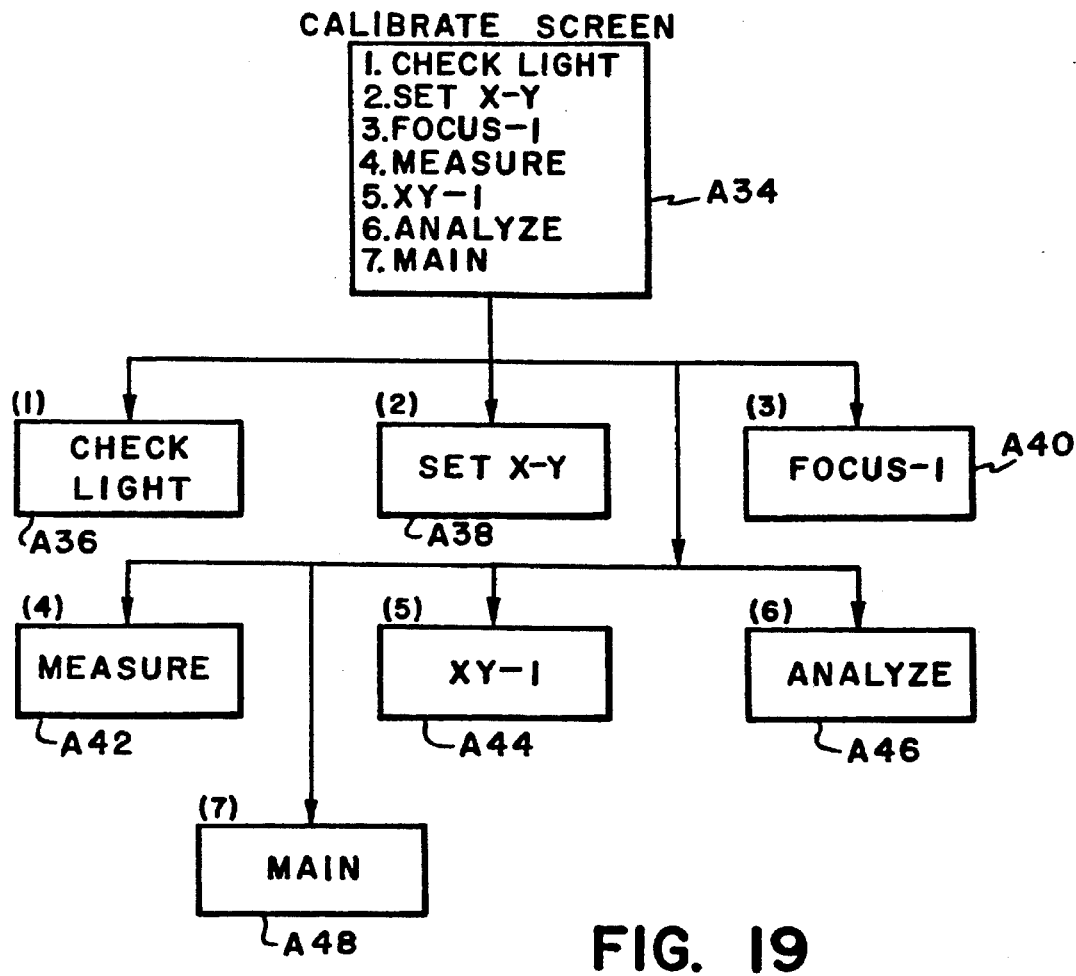
FIG. 19 is a functional flow chart of the calibrate menu of the calibrate screen illustrated in FIG. 17.

The calibrate screen A14 displays the calibrate menu A34 illustrated in FIG. 19. The calibrate menu A34 provides seven choices which include 1) a check light function A36, 2) a set XY function A38, 3) a focus function A40, 4) a measure function A42, 5) an XY-1 function A44, 6) an analyze function A46, and 7) a main function A48.

Figure 20:
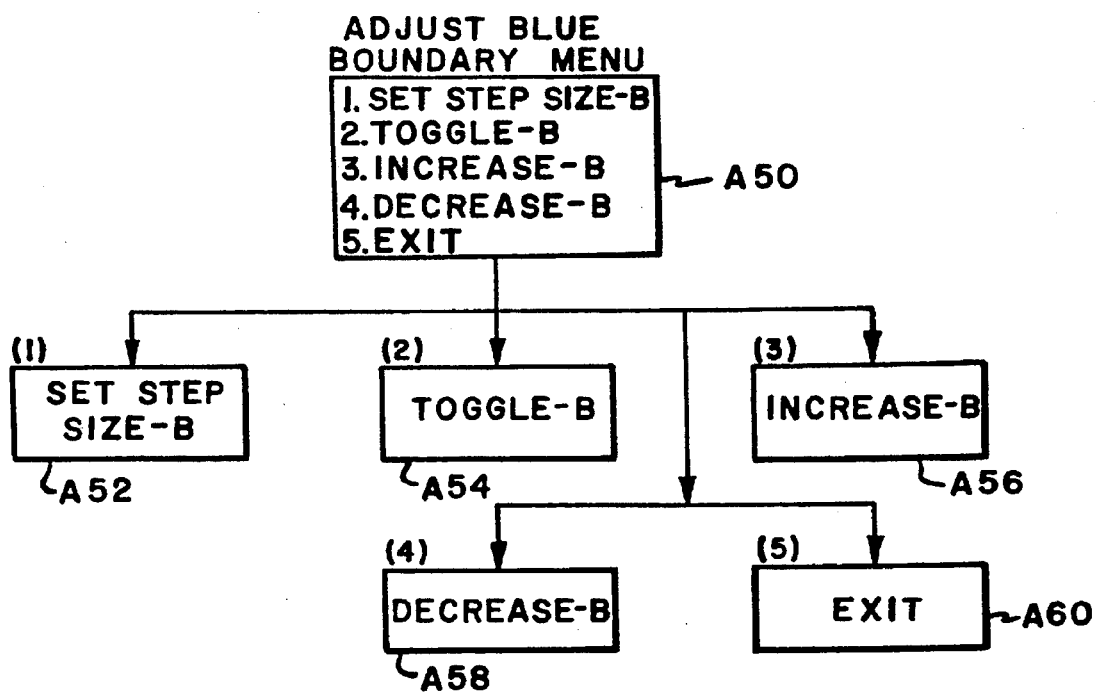
FIG. 20 is a functional flow chart of the adjust blue boundary menu of the adjust blue boundary screen illustrated in FIG. 17.

The adjust blue boundary screen A18 displays the adjust blue boundary menu A50 illustrated in FIG. 20. The adjust blue boundary menu A50 provides five choices which include 1) a set step size-B function A52, 2) a toggle-B function A54, 3) an increase-B function A56, 4) a decrease-B function A58, and 5) an exit function A60.

Figure 21:
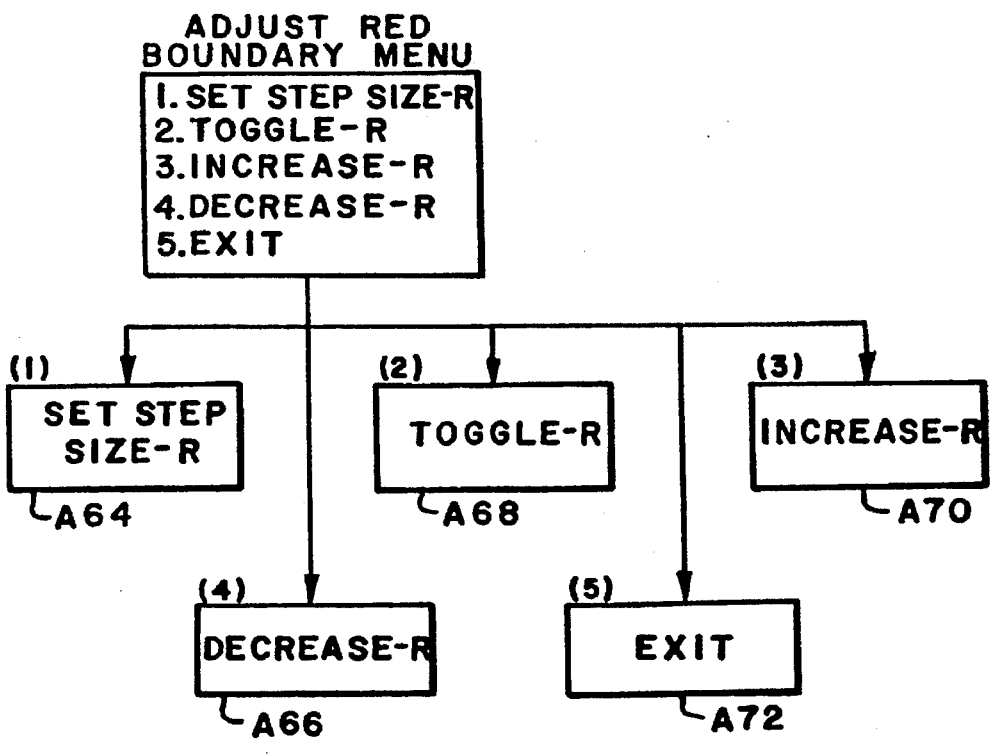
FIG. 21 is a functional flow chart of the adjust red boundary menu of the adjust red boundary screen illustrated in FIG. 17.

The adjust red boundary screen A20 displays the adjust red boundary menu A62 illustrated in FIG. 21. The adjust red boundary menu A62 provides five choices which include 1) a set step size-R function A64, 2) a toggle-R function A68, 3) an increase-R function A70, 4) a decrease-R function A66, and 5) an exit function A72.

Figure 22:
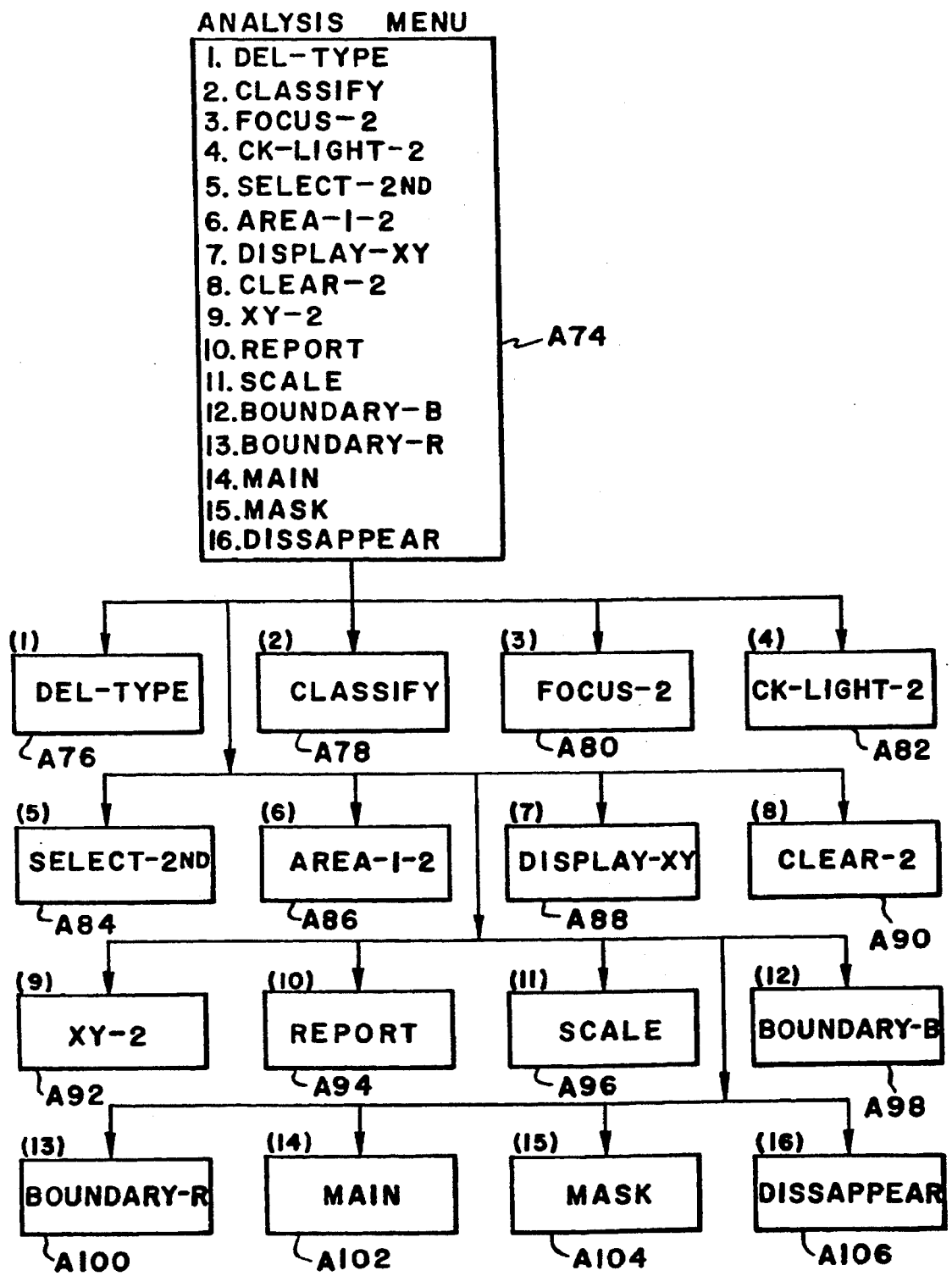
FIG. 22 is a functional flow chart of the analysis menu of the analysis screen illustrated in FIG. 17.

The analysis screen A16 displays the analysis menu A74 illustrated in FIG. 22. The analysis menu A74 provides sixteen choices which include 1) a del-type function A76, 2) a classify function A78, 3) a focus-2 function A80, 4) a CK-light function A82, 5) a select 2nd function A84, 6) an area 1-2 function A86, 7) a display XY function A88, 8) a clear function A90, 9) a XY-2 function A92, 10) a report function A94, 11) a scale function A96, 12) a boundary-B function A98, 13) a boundary-R function A100, 14) a main function A102, 15) a mask function A104, and 16) a disappear function A106.

The label function allows a user to enter information regarding patient identification, accession number, and DNA conversion number. The DNA conversion number is the number that the first and second peak masses are divided by to get the first and second peak indexes. Initially, the number is set to a standard 7.18 picograms/cell for normal human cells. However, the apparatus may be used to measure non-human cells and the index may be changed to that desired. The DNA index number must be greater than or equal to 1.0 and less than or equal to 99.99. If the conversion number is not within that range, the user is not allowed to select the analyze option in either the main or the calibration screens.

The three lines of information entered during the label function will appear on every screen except the X, Y field coordinate screen. The label operation is exited by pressing either the enter or escape key. Pressing the enter key will save any changes that were made to the three lines of information. Pressing the escape key will ignore any changes that were made to the three lines. The information stored during the label function will not be saved when the program is exited.

Figure 15:
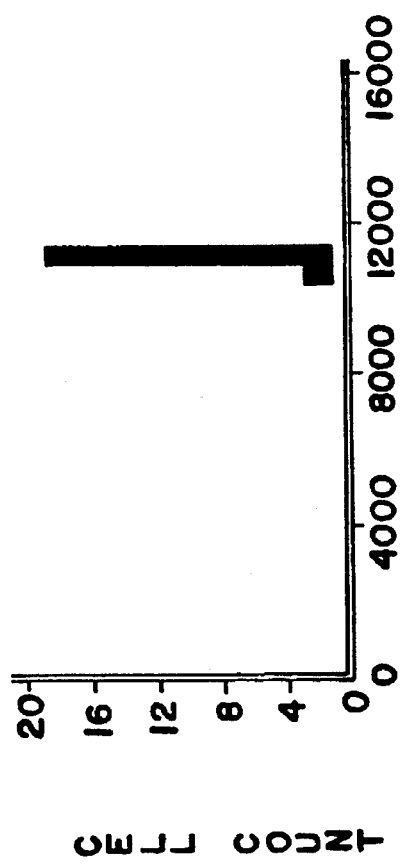
FIG. 15 is a pictorial representation of the calibration screen which appears on the instruction monitor illustrated in FIG. 1.

Selecting the calibrate function will cause a change of the display on instruction monitor 62 from the main screen to the calibration screen illustrated in FIG. 15. The calibration screen whose options are shown in FIG. 19 are those necessary to perform calibration of the instrument for optical density and for staining factor on the control cells. A calibration of the apparatus 11 is to be performed every time a new slide is selected to normalize the light level and staining factor.

Figure 16:
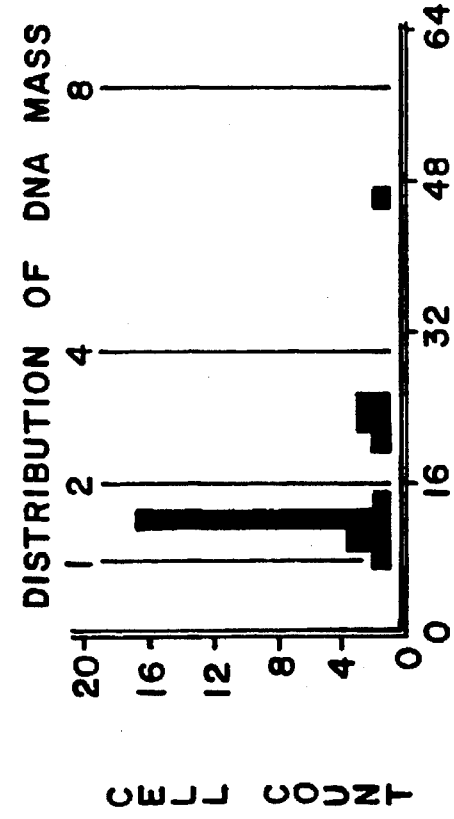
FIG. 16 is a pictorial representation of the analysis screen which appears on the instruction monitor illustrated in FIG. 1.
Figure 17:
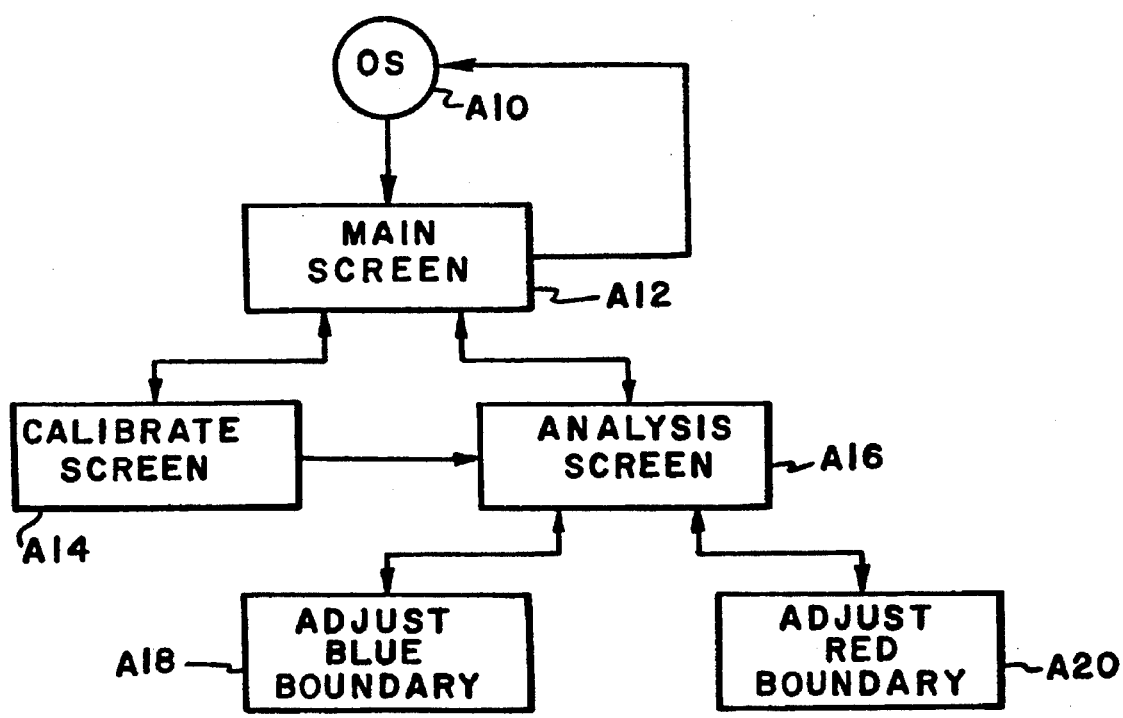
FIG. 17 is a system flow chart of the analysis system screen architecture of the image analysis system illustrated in FIG. 1.

Selecting the analyze function will cause a change of the display from the main screen on monitor 62 to the analysis screen as illustrated in FIG. 16. The analysis screen contains the menu for the functions that are necessary to perform data acquisition and DNA measurements on the specimen cells. These functions are more fully set forth in FIG. 22. Three criteria must be met in order to select the analyze function. First, the set light function in the calibration screen must have been successfully performed at least once. The set light function is successful when the current image is blank and the light level is between 129 and 131. Secondly, the calibration control cell count must be between 50 and 512. Finally, the DNA conversion number must be greater than or equal to 1.0 and less than or equal to 99.99.

The exit function allows the user to terminate the operation of the program from the main screen. Pressing the escape key is the same as selecting the exit function. When the exit operation is specified, either by selecting exit or pressing escape, the user will be asked to confirm his command to exit. To accept the confirmation, the user selects the yes key. To reject the confirmation, he selects the no key or presses the escape key.

The options of the calibration menu will now be more fully explained. The set X, Y of function A38 provides the setting of the origin for the slide X, Y coordinate system. This function sets the current image or field location as the origin by zeroing a pair of location registers in the software. Generally, the microscope platform 51 is moved until a easily recognized landmark is visible, such as cross 53. This landmark is then used to rezero the coordinate system to provide a means of relocating previously measured fields. The set X, Y function is used every time a new slide is selected. If the set X, Y function has not been executed, then the X, Y functions of the calibration and analysis screens and the functions in the X, Y field coordinates screen will not work properly. The set X, Y function can only be used when the calibration control cell count is equal to zero. If the microscope platform 51 is being moved when the set X, Y operation is in execution, then the coordinate origin will be in error. The program provides a message on the screen to notify the operator when the set X, Y operation is successful. In response to the function not being successful, the operator merely reselects set X, Y from the menu and attempts the function again.

The measure function A42 is used to perform the control cell or control object calibration for normalizing the staining factor. When the measure function is selected, the camera image acquisition will stop and the cursor 170 on the calibration screen will move to the words "measure operations" in FIG. 15. When the cursor 170 is at this location, the user can specify measure operations by activating the numeric lock key. An identifier such as a magenta colored box will be placed around an identified cell object. By using a number of key operations, the operator can perform an interactive selection and rejection process which will be more fully explained hereinafter.

During control cell calibration, the operator moves the microscope stage by turning the conventional X and Y knobs 12 and 17 (FIG. 1) to shift the control cell objects 40 into view on the image monitor 37. When an individual cell object 40 is within a box or identifier border 75, the operator presses a key on the keyboard 36 to enter measurement of the summed optical density for that control cell object. After a suitable number of control cell objects have been analyzed, the operator will be provided with a histogram such as shown in FIG. 15 on the instruction monitor 62 which shows the operator the control cell object ploidy distribution as having a relative quantity of DNA. Internally within the system control 22, the summed relative optical density values actually measured for the control cell objects are compared to a predetermined standard or reference amount of DNA which the control cells are known to have. The actual summed optical density found by the operator is divided into the stored reference DNA value to provide a factor by which to adjust the extinction coefficient for deviations in the stain from a perfect staining.

The XY-1 function A44 when selected displays on the calibration screen the X, Y coordinates of the current image or field on image monitor 37. The coordinates will be continuously displayed until the user presses a key (except CTRL, ALT, or SHFT). Thus, if the same origin for the slide 14 was set, the operator can, by positioning the platform 51 and watching the coordinates change, find the same image which was previously recorded. The set X, Y function A36 must have been successfully performed previously in order for the X, Y function to be selected.

The FOCUS-1 function A40 provides color enhancement to the image so that the user can perform more precise focusing of the image. The system control 22 automatically provides different colors for gradations in grey level in the image. The operator then adjusts the focusing means of the microscope 15 until the object being focused on, for example an edge of the border 54, shows a clear color demarkation. This is an indication that the two separate levels or grey scale of the edge are in focus. This is much more difficult without color because the two grey levels may be close together and undiscernible without the color enhancement. The set light function A30 must have been successfully performed at least once in order to select the focus function. To restore the image to its original color, the focus function is selected a second time. If the color enhanced image is present when the user selects the measure function, the image will automatically be returned to its original color.

Selecting the analyze function will change the display from the calibration screen to the analysis screen. The analysis screen provides a menu of functions shown in FIG. 22 which are necessary to perform the DNA measurements on the cellular material. Three criteria must be met in order to select the analyzed function. First, the set light function in the calibration screen must have been successfully performed at least once. Secondly, the calibration control cell count must be between 20 and 512. The analyze function in the calibration menu works the same way as the analyze function in the main menu.

The analyze function options in the analysis menu are more fully shown in FIG. 22.

The check light-2 function A82 calculates the light level of the current image. The light level value is displayed on the analysis screen by the words "light level" in FIG. 16.

The select-2nd function A84 allows the user to select the second peak on the histogram displayed on the analysis screen. The mass, DNA index, and the area of the second peak are displayed on the screen under the words "second peak." The select-2nd function cannot be selected when the shown cell count is equal to zero. The shown cell count is displayed by the word "shown." After the select-2nd function has been selected, the cursor will move to a set of arrows and the current second peak location on the histogram will be highlighted in yellow. Initially the right most histogram data location is chosen as the second peak. Selecting the left arrow moves the second peak location to the left and the user selects the right arrow to move the second peak location to the right. Every time an arrow is selected, the current peak data on the screen will be updated.

Below the histogram horizontal axis, one of three symbols will appear underneath the second peak location. A "less than" symbol will appear if the second peak lies in area one. A "greater than" symbol will appear if the second peak lies in area two. An up arrow symbol will appear if the second peak lies in neither area one nor area two. The reason for the three symbols is so that the second peak location can be identified after the select-2nd operation is exited. The vertical yellow line disappears once the select-2nd function is exited. The user presses the ESC key to exit the select second operation. The second peak data will also be automatically cleared when one of the following analysis screen functions is selected: clear, report, scale, or main.

The classify function A78 allows the user to classify the cells or objects in the current image. After the classify function has been selected, the user will be asked to confirm the operation. To accept the confirmation, the user will select the yes key, and to reject the confirmation, the user will select the no key or press the ESC key. If the classification function is confirmed, camera acquisition stops and the cursor will move by the words "classify operation". When the cursor is at this location, the user can specify the classify operations by activating the numeric lock to enable these functions. As was the case in the measure function, a magenta colored box will be placed around a current cell and the operations allow the user to move this cell identifier through the image to identify and classify the cells therein.

The display X, Y function A88 will change the display from the analysis screen to the X, Y field coordinates screen. The X, Y field coordinate screen will display the X, Y coordinates of the first 512 images that have been classified and stored. Also, the screen contains the functions that allow the sorting of the image fields by coordinates. The set X, Y function in the calibration screen must have been successfully performed before the display X, Y function is selected.

The X, Y field coordinate screen has several functions. One of the functions, "nearest" sorts the X, Y coordinates according to the distance from the current X, Y field position. The X function will sort the X, Y coordinates according to the X coordinate value. If there is a tie, then the Y coordinate value will determine the sort order. Similarly the Y function will sort the X, Y coordinates according to the Y coordinate value. If there is a tie, then X coordinate value will determine the sort order. The "field#" function will sort the X, Y coordinates according to the coordinates field number. The field number is the order in which the images were classified.

The page up function allows the user to display the previous page of X, Y coordinates, if any, and the page down function allows the user to display the next page of X, Y coordinates, if any. The exit function changes the display from the X, Y field coordinate screen to the analysis screen. Pressing the escape key is the same as selecting the exit function.

Selecting the X, Y function displays the X, Y coordinates of the current field. The coordinates will be continuously displayed until the user presses a key (except CTRL, ALT, and shift). The set X, Y function in the calibration screen must have successfully been performed before the X, Y function is selected. The X, Y function in the X, Y field coordinate screen works the same way as the X, Y function in the calibration and analysis screens.

The clear-2 function A90 will clear all analysis related areas of data. After the clear function has been selected, the user will be asked to confirm the clear operation. To accept the confirmation, the user selects the yes key, or to reject the confirmation, the user will select the no key or press the ESC key.

The focus-2 function A80 provides color enhancement to the image so that the user can perform more precise focusing of the image. The focus-2 function in the analysis screen works the same way as the focus function in the calibration screen previously described.

The area 1-2 function A86 allows the user to specify two areas in the histogram displayed in the analysis screen. The purpose of this function is to identify the cell counts in certain areas in the histogram. The area 1-2 function cannot be selected when the shown cell count is equal to zero. The cell counts are displayed at the lower right portion of the screen. After area 1-2 is selected, the cursor will move to a row of numbers that is below the histogram horizontal axis. The row of numbers allows the user to specify the locations of area 1 and area 2. The user types a "1" to specify that the current histogram position belongs to area 1. The user types a "2" to specify that the position belongs to area 2. The user types a "0" to specify the current histogram position belongs to neither area 1 nor 2. The user is allowed to specify an area 1 without an area 2, but cannot specify an area 2 without an area 1. When both areas are specified, area 1 must be specified to the left of area 2. The area must be specified as continuous. To exit the area 1-2 function, the user presses the enter or ESC keys. If the user presses the enter key, area 1 of the histogram will be highlighted in green and the area 2 will be highlighted in magenta. The area cell counts will also be displayed. Pressing the ESC key will cause the program to disregard any of the changes that were made. Area 1 and area 2 data will automatically be cleared when one of the following functions is selected: classify, clear, reports, scale or main.

Figure 14:
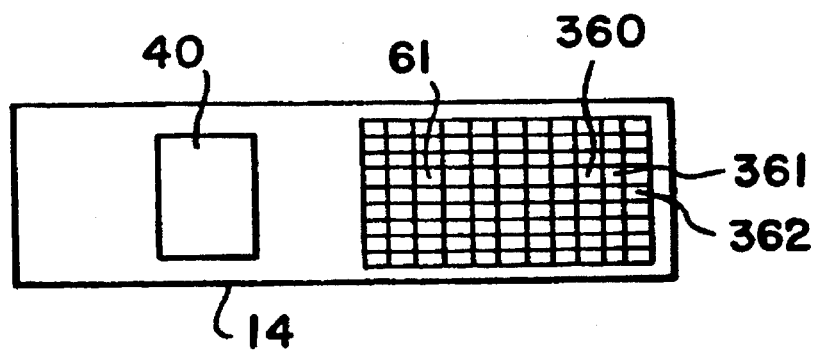
FIG. 14 is a pictorial representation of the many optical fields on the slide illustrated in FIGS. 5 and 6.

The analysis function is more fully described with respect to FIGS. 13 and 14. The operator will select a number of field locations 360, 361, and 362 in the slide specimen area 58 for analysis. The operator will adjust the X and Y knobs 12 and 17 for the microscope stage 51 to move these fields into view on the image monitor 37 a first field of specimen cell objects to be analyzed for DNA content as well as for cell morphology if desired (FIG. 13). The program will place a box, for example at 300, over a particular specimen cell object being displayed on the monitor 37 and then the operator will use a key to cause the scanning of the pixels (picture elements) of the specimen object to classify the cell in a manner similar to that disclosed in U.S. Pat. No. 4,453,266 to give summed optical density for the cell specimen object i.e., a stained cell nucleus, as well as its area, its roundness, and other classification information.

Also, the operator has on the keyboard 36 several cell classification keys to be manually operated and the operator depresses one of the keys of a known category such as a type 0 normal cell; a type 1 cancer cell; a type 2 cancer cell; a type 3 cancer cell; and etc. On the monitoring screen 62 there will be an analysis histogram displaying the DNA content of the cells in the field. The operator selects a number of cells in each field or area and then moves the microscope stage to position a number of different fields of specimen cells into view and takes and analyzes a number of these specimen cells until the operator feels he has enough cells for a representative sample.

A histogram, will at this time be displayed on the instruction monitor screen 62 which shows the number of cells of a particular DNA content and shows the DNA content averages for each of the reference peaks, such as shown in FIG. 16. By depressing a print key, on the keyboard 36 the operator may print out the histogram shown in FIG. 16 on the printer 38. The data for the specimen cells is also stored internally within the system control 22 for later recall and comparison with data of any new specimen from the same patient for analysis relating to the progress or regression of a patient.

The operation of the manual classification for the analysis function will be now more fully described with respect to FIG. 13 where there is shown a visual field which has been previously stored in the instrument. The field contains a number of cell objects which are to be classified and measured as to DNA content. When the program initially comes into this mode of operation, the first object in the field will be identified by scanning the pixels of the field in a raster like manner until a cell object is recognized. Once a cell object is recognized, an identification means such as box 300 is drawn around the object. This provides a visual identifier for the operator to determine which cell object is presently being measured. In addition to the measurement, the operator is provided with a number of options from the analysis menu. The primary option that an operator has is to classify a current object in block A78. He accomplishes this by pressing one of the numeric keys 0 through 5 which automatically puts the cell object of the identifying box 300 into the classification selected. If the object identified is debris, not an abnormal cell, or not an identifiable cell object, the operator can reject the current object by selecting a 9 on the keyboard as indicated.

After the classification or rejection of the object in box 300, the operator can move the identification box to the next unmeasured object. An operator accomplishes this by pressing the keys CTRL/F2 which causes the program to erase the box 300 and search for the next identifiable cell object. This cell object is found, and then another identifying box 302 is drawn around it to indicate to the operator the function has been accomplished. In this manner, the entire group of cell objects can be classified and measured or rejected by repeating this process. In this manner, the program steps through the analysis procedure from object 300 to 302, 304, 306, 308, 310, etc.

Further, if one of the cell objects to be classified does not look like the operator thinks it should and, it cannot be put in one of the previous classifications, or for some other reason the operator believes he has classified a previous object by mistake, then by pressing CTRL/F1, he can move the identifying box back to the previously measured object. After identifying all cell objects in the particular field being displayed, the operator has the option of going to another field by manipulating the X, Y positioning mechanism to provide more cells for the particular analysis.

When the operator has determined that enough cell objects had been analyzed, he may either terminate the analysis function by pressing either the enter key or escape key. If he terminates the analysis function by pressing the enter key, then the data assembled from each of the measurements will be saved. However, if the analysis function is terminated by pressing the ESC key, then the data will not be saved.

The report function A94 allows the user to specify which cell classifications are to be included in the histogram shown on the screen of the instruction monitor 62. After the report function has been selected, the cursor can be moved to an option list which will allow the operator to specify the cell types. The following table specifies which key the operator presses in order to select a particular cell type.

| CELL TYPE | KEY |
| --- | --- |
| normal | 0 or n |
| 1 | 1 |
| 2 | 2 |
| 3 | 3 |
| 4 | 4 |
| lymphocyte | 5 or L |

Any combination of the types for the report data is allowed. The program will ignore any other characters than those listed in the table. The operator exits the report operation by pressing the enter or escape key. If the operator presses the enter key, he will change the types of cells in the histogram to those which were specified. However, if the escape key is selected, the program will ignore any changes that were made and return normally. The function area 1-2 data and the second peak data will automatically be cleared when the report operation is performed.

The scale function A96 allows the operator to change the scale of the horizontal axis of the histogram provided on the analysis screen. There are three scales to choose from, 0–16, 0–32, and 0–64. If the scale function is selected when the current scale is 0–16, then the new scale will be 0–32. If the scale function is selected when the current scale is 0–32, then the new scale will be 0–64. Likewise, if the scale function is selected when the current scale is 0–64, then the new scale will be 0–16. In this function the area 1, area 2, and second peak data will automatically be cleared when the scale operation is performed.

The boundary functions A98, A100 will change the display on instruction monitor 62 from the analysis screen to the respective adjust boundary screen. The adjust boundary screen contains functions that are necessary to change the cell boundary, i.e., threshold. While addressing the boundary screen, camera image acquisition will be halted.

The set step size function of FIGS. 20 and 21 allows the operator to change the amount by which the boundary will change when one of the arrow keys is selected. The value must be in the range of 0–128. After the step size is selected, the cursor will move to the location on the screen where the user can type in a new step size value. To exit the step size function, the enter or escape keys are used. Pressing the enter key will save the step size change where pressing the escape key will ignore any change that was made. Initially, the step size value is equal to one.

The increase function A56, A70 will increase the cell boundary by the value of the step size and the decrease function A58, A66 will decrease the cell boundary by the value of the step size. The exit functions A60, A72 change the display from the adjust boundary screens back to the analysis screen. Pressing the escape key is the same as selecting the exit function.

In general, an interactive data collection and analysis scheme is used by the apparatus for the collection of specific parameters for both the calibration cell objects and the specimen cell objects. Each field which is selected is displayed on the image monitor 37 and either the measure operation of the calibration screen or the classify operation of the analysis screen is chosen.

A software flow chart of a subroutine provides the interactive operations for the calibrate key operations and the analysis key operations, FIGS. 15 and 16 and is illustrated in the referenced Bacus application. When the operator selects either the measure operations or the classify operations, this program is called to generate the selection process for both the calibration cell objects and the specimen cell objects. The program begins by performing a raster scan of the stored image pixel by pixel until it finds a pixel greater than the threshold value. If no pixel is found which is greater than the threshold, a determination of whether the scan is complete is made. If not, the scan is continued until all pixels in the image field are tested. After all pixels have been tested, the scan parameters are reset and the cell object array updated.

At the time an image pixel is determined to be greater than the threshold, the program will label the object. The operation of labelling will now be more particularly described. The individualized cell objects in the digitized image are located by a scene analysis technique in which the raster scan is made of the digitized image to locate any pixel above the critical threshold. The technique then performs a four neighbor analysis of adjacent pixel elements and continues in a recursive manner locating "neighbors of the neighbors" which are above the threshold until the entire region of a cell object is defined. This technique is preferred to other scene analysis techniques, such as local boundary found from a gradient image, because it is fool proof in distinguishing the true region of a cell, particularly those cells having irregular or spiculed projections.

The four pixels (top, bottom, right side, and left side) surrounding the initially located pixel which are contiguous therewith are examined sequentially to identify the next pixel with an optical density or gray level value above the threshold. For instance, if the pixel located above the first pixel is not above the threshold, it is discarded from the labelling routine. The next pixel (right side) in a clockwise direction is then examined and may be above the threshold. If so, that pixel is then identified and stored in memory with the pixel as being a portion of the region of a cell. Next the address and density of the pixel found is stored in a pushdown list and the four neighboring pixels of that pixel are examined in the same clockwise order. This continues in a recursive manner until no neighbors are found above a threshold for a particular pixel. At this point the prior pixels on the pushdown list are reexamined to continue the neighbor search process until the entire number of pixels defining a region, i.e., the cell object has been identified. Thus, each of the pixels above the threshold of the region are identified and a complete enclosed region has been defined for a cell.

Once a cell object is labelled, a cell object table is set up for the object. The table lists the address of its entry point pixel, the number of pixels in the object, the X, Y points for the minimum and maximum points of the object, a count of the pixels in the perimeter of the object, the sum of the optical density of the object pixels, any classification provided for the object, and the X, Y coordinates of the field to which the object belongs. A plurality of the cell object tables comprise a temporary array, called a field array, which is used to store the interactive data developed for the present field image under consideration.

Next, a box or identifying border is placed around the object using the X, Y limits. This mode identifies a particular object in the field for the operator. A key handler is entered to obtain a key press from the operator to determine which of the key functions of the classification function are to be accomplished. The key handler further determines which operation, either for calibration or analysis, is to be performed and only those keys which are associated with the present mode are enabled, all others are locked out. Once a key has been obtained, the program will determine which function was selected and the progress of the routine.

Keys 0–5 as detected provide for the acceptance of a calibration object or the classification of a specimen object.

If such key is detected, then the object is colored (red) to indicate to the operator that it has been accepted or classified. The operator classifies the cell objects into different categories based upon visual clues such as morphology and the optical markings. The cells for analysis can be classified into a normal class 0, or one of several abnormal classes 1–5. The data class of the object is stored in its place in the associated object data table. Calibration objects are classified as type 0 or normal. The program then returns to where the image scan registers are incremented to scan the field for the next object.

Alternatively, if the key press was a 9 as this means either a calibration cell object was rejected or a current specimen cell object was rejected. Thus, the rejected cell object is colored in a different color (white) than an accepted or classified cell object, and the program returns to the scanning routine to find another object. Coloring the cell object alerts the operator that the object has been analyzed in this field, coloring the object another color differentiates the object from an accepted or classified cell objects.

If, however, the key press is a CTRL/F1, then the operator desires to move the identifying box to the last previously measured object. The program will then interrogate the field array to find the last object pointer. This pointer is used to create the box around the previous cell object before getting another key press. By using a series of CTRL/F1 keys the operator may selectively move the identifying box from the previously measured cell object to the previously measured cell object in a reverse direction. If, after the box is placed around a particular cell object, the operator desires to reclassify that cell object, he then has the option of classifying it with the keys 0–5 in block A326.

The identifying box may be moved to the next unmeasured cell object by selecting the key CTRL/F2. The key, if found, immediately returns the program control to the image scan entry. The effect of this operation is to allow the operator to skip the present cell object and move the identifying box to the next cell object without either rejecting or accepting the present cell. A series of CTRL/F2 presses will move the box forward through the cells without measuring them.

If all of the cell objects in a particular field appear normal as specimen cells, or as is generally the case with control cells they are acceptable, the operator may want to classify them all automatically. To accomplish this, an operator presses the key CTRL/F3. This key press is detected and transfers control to where the automatic mode flag is set. The program then returns to the entry of the image scan. However, instead of going through the normal sequence of placing a box around the next object and waiting for a key press, the program will loop to automatically classify the rest of the cells of a field.

Another option that the operator can select is the cell cutting function which is entered by pressing the key CTRL/F4. This key is detected and transfers control to the cell cutting function operation. When the CTRL and F4 keys are pressed, the user enters the cell cutting mode. While in this mode, the user is permitted to make cut lines inside the identifier box. The operator cannot make a cut line over a pixel that belongs to a measured or a rejected cell. A measured cell is a cell that has been classified as type 0, 1, 2, 3, 4, or 5. Numeric lock must be activated in order to perform a cell cutting operation. A cross hair is located where the cut is to take place. The following table lists the cell cutting operations that can be performed plus the key that must be pressed in order to select the desired operation. The function allows the splitting of overlapping cells by artificially making a perimeter between two areas, a cut. Thus, the labelling routine will only label one area as a cell object.

| (KEY) | (ACTION) |
|---|---|
| 0 | Turn splitting on and off |
| 1 | Go down and left one step |
| 2 | Go down one step |
| 3 | Go down and right one step |
| 4 | Go left one step |
| 5 | Go to the center of the box |
| 6 | Go right one step |
| 7 | Go up and left one step |
| 8 | Go up one step |
| 9 | Go up and right one step |
| ENTER | Re-do last step (up to 100 pixels) |
| ESC | Exit cell splitting mode |

A step is three pixels. When beginning a new cut, the first pixel will not be cut. For operation 5, the cross hair will not move if the center pixel belongs to a measured or rejected cell.

After the cell cutting is performed, the scanner registers are set to the entry point of the particular object cut. The program then returns to the scan entry. Because the cell object has the same entry point but a different perimeter, the labelling routine will label the cell object as now cut.

Another option that the operator has is the ability to select any object within a field. The selection of this mode is accomplished by pressing the CTRL/F5 key.

When the CTRL and F5 keys are pressed, the user enters the selection mode. Numeric lock must be activated in order to perform a selection operation. A cross hair will appear at the current selection point. The following table lists the selection operations that can be performed plus the key that must be pressed in order to select the desired operation.

| (KEY) | (ACTION) |
|---|---|
| 0 | Select cross hair movement step size [5 or 15] |
| 1 | Go down and left one step |
| 2 | Go down one step |
| 3 | Go down and right one step |
| 4 | Go left one step |
| 5 | Go to the center of the image |
| 6 | Go right one step |
| 7 | Go up and left one step |
| 8 | Go up one step |
| 9 | Go up and right one step |
| ESC | Exit selection mode |

When the selection mode is exited, the box will move to the first unmeasured cell after the selection point. If there are no cells after the cross hair, the box will go to the next unclassified cell.

After the object is selected by the above described technique, the scanner registers are set to the entry point of that particular object in block A348 and the program returns to the scan entry in block A300. This creates the identifier box around the object using its X, Y limits and provides the operator with the option of then pressing another key and performing other measurements and classifications on that selected object.

Another function is provided by key CTRL/F6. This feature provides an operator with the ability to move the identifier box forward by reading the next cell object pointed to and then drawing around the box the chosen object in block A313. The keys CTRL/F1, CTRL/F2 thereby allow an operator to quickly revise previous cell classification by stepping forward and backwards, respectively, through the pointers of the previously measured cells.

When the enter key is sensed, the cell object array is updated with the present field array to store all of the data collected for the particular objects in the field. Alternatively, the sensing of the escape key returns the program immediately to the place in the software where it was called.

It will be appreciated that the illustrated control 22 has been programmed to do the cell classification and optical density analysis. Such classification and analysis is similar to that outlined in U.S. Pat. No. 4,453,266 for the classification of red blood cells and the present invention can be particularly useful in the analysis of red blood cells wherein the optical density of the hemoglobin content is measured rather than the DNA content as above described. As common in red blood cell analysis, the red blood cells need not be stained for image enhancement so that the staining calibration step may be eliminated for red blood cells when using the specific wave length of light specified in the aforementioned Bacus patents.

A further use of the present invention is to provide a precise measurement of hemoglobin in actual picograms for calibrating other instruments such as a Coulter counter. In such a process, the control blood cells 40 will have a known predetermined hemoglobin value and the specimen blood cells 52 of unknown hemoglobin value will be placed on the specimen area 58. Then the apparatus will be calibrated to show the histogram for the hemoglobin content of the specimen cells 52.

It will also be appreciated that the various calibration steps may be eliminated or combined and done simultaneously rather than done in the order and in the sequence and in the manner described for the preferred embodiment of the invention in making a DNA analysis.

While a preferred embodiment of the invention has been illustrated, it will be obvious to those skilled in the art that various modifications and changes may be made thereto without departing from the spirit and scope of the invention as defined in the appended claims.

What is claimed is:

1. An apparatus for the analysis of a plurality of cell objects having nuclear DNA on a support which have been optically enhanced, wherein the enhancement includes the enhancement of an area of the nuclear DNA of the cell objects by a Feulgen staining technique and the enhancement of location and content of specific protein sites of the cell object by an immunohistochemical staining technique;

said apparatus comprising:

means for magnifying an image of the cell objects:

means for filtering said magnified image at a band of wavelengths where said areas of DNA staining are relatively opaque when compared to said areas of immunohistochemical staining to provide a first filtered image;

means for filtering said magnified image at a band of wavelengths where said areas of immunohistochemical staining are relatively opaque when compared to said areas of DNA staining to provide a second filtered image;

means for digitizing and storing said first filtered image and said second filtered image;

means for combining said first filtered image with said second filtered image such that cell objects having areas of immunohistochemical staining are marked;

means for displaying said combined image to an operator;

means for classifying each of the cell objects into one of several classifications based on morphological criteria of the areas of DNA staining and marked areas of immunohistochemical staining; and means for measuring DNA mass of each of said cell objects and classifications of cell objects.

2. An apparatus as set forth in claim 1 wherein said first means for filtering includes:

an optical bandpass filter having a passband in the range of 620 nanometers.

3. An apparatus as set forth in claim 2 wherein:

said passband is approximately 20 nanometers wide.

4. An apparatus as set forth in claim 1 wherein said second means for filtering includes:

an optical bandpass filter having a passband in the range of 480 nanometers.

5. An apparatus as set forth in claim 4 wherein:

said passband is approximately 20 nanometers wide.

* * * * *